US008600479B2

(12) United States Patent
Dalke et al.

(10) Patent No.: US 8,600,479 B2
(45) Date of Patent: Dec. 3, 2013

(54) GUIDANCE AND IMPLANTATION OF CATHETERS

(75) Inventors: William D. Dalke, Aurora, CO (US); Kevin Lillehei, Englewood, CO (US); Thomas A. Jellison, Coventry, RI (US); Michael J. Gerber, Denver, CO (US); James E. Matsuura, Fort Collins, CO (US); Stephen L Warren, Fort Collins, CO (US)

(73) Assignee: Peak Biosciences, Inc., Fort Collins, CO (US)

( * ) Notice: Subject to any disclaimer, the term of this patent is extended or adjusted under 35 U.S.C. 154(b) by 733 days.

(21) Appl. No.: 12/531,808

(22) PCT Filed: Mar. 20, 2008

(86) PCT No.: PCT/US2008/003711
§ 371 (c)(1),
(2), (4) Date: Mar. 11, 2010

(87) PCT Pub. No.: WO2008/115566
PCT Pub. Date: Sep. 25, 2008

(65) Prior Publication Data
US 2010/0222668 A1    Sep. 2, 2010

Related U.S. Application Data

(60) Provisional application No. 60/895,916, filed on Mar. 20, 2007, provisional application No. 60/917,226, filed on May 10, 2007.

(51) Int. Cl.
*A61B 5/05*    (2006.01)

(52) U.S. Cl.
USPC ........... 600/424; 600/433; 600/434; 600/435; 600/466

(58) Field of Classification Search
USPC .............................. 600/424; 604/43, 65, 272
See application file for complete search history.

(56) References Cited

U.S. PATENT DOCUMENTS

| 2,245,350 A | 6/1941 | Marshall, G. R. |
|---|---|---|
| 4,235,506 A | 11/1980 | Saito et al. |

(Continued)

FOREIGN PATENT DOCUMENTS

| WO | WO-94/04220 A1 | 3/1994 |
|---|---|---|
| WO | WO-99/07276 A2 | 2/1999 |

(Continued)

OTHER PUBLICATIONS

International Application Serial No. PCT/US2008/003582, Search Report mailed Jul. 2, 2008, 6 pgs.

(Continued)

*Primary Examiner* — Tse Chen
*Assistant Examiner* — Joel F Brutus
(74) *Attorney, Agent, or Firm* — Schwegman Lundberg & Woessner, P.A.

(57) ABSTRACT

A catheter system adapted for navigating, guiding and implanting a catheter or a plurality of catheters in a spatially-defined implantation within the tissue of a patient is provided. The system can include a tissue navigation system and a probe to inform the navigation system to guide emplacement of the catheters within a target tissue. The probe can provide images, such as fiberoptic visual images, or ultrasound images, or can provide radiolocation data, to guide the catheter emplacement. The catheters supply a pressurized liquid including a bioactive agent, such as can be used in the treatment of cancer, for example 123I- or 125I-IUDR. The system and methods provided can be used in the treatment of locally advanced tumors, such as cancers of the brain, head or neck, esophagus, prostate, ovary, liver, pancreas, bladder or rectum.

59 Claims, 17 Drawing Sheets

(56) References Cited

U.S. PATENT DOCUMENTS

| | | | |
|---|---|---|---|
| 4,994,033 A * | 2/1991 | Shockey et al. | 604/101.02 |
| 5,077,034 A | 12/1991 | Kassis et al. | |
| 5,221,256 A * | 6/1993 | Mahurkar | 604/43 |
| 5,354,279 A | 10/1994 | Hofling | |
| 5,465,711 A * | 11/1995 | Moll et al. | 600/207 |
| 5,720,720 A | 2/1998 | Laske et al. | |
| 6,068,650 A * | 5/2000 | Hofmann et al. | 607/2 |
| 6,283,947 B1 | 9/2001 | Mirzaee | |
| 6,428,504 B1 * | 8/2002 | Riaziat et al. | 604/65 |
| 6,486,146 B1 | 11/2002 | Zamoyski | |
| 6,610,841 B1 * | 8/2003 | Warren | 536/25.3 |
| 6,627,176 B2 | 9/2003 | Perkins | |
| 6,703,050 B1 | 3/2004 | Brewer et al. | |
| 2001/0007933 A1 * | 7/2001 | Lesh et al. | 604/272 |
| 2001/0009970 A1 | 7/2001 | Chornenky et al. | |
| 2001/0031941 A1 | 10/2001 | Edwards et al. | |
| 2002/0002349 A1 | 1/2002 | Flaherty et al. | |
| 2002/0082559 A1 * | 6/2002 | Chang et al. | 604/164.09 |
| 2002/0123719 A1 | 9/2002 | Lavi et al. | |
| 2002/0133057 A1 | 9/2002 | Kukuk | |
| 2002/0133173 A1 * | 9/2002 | Brock et al. | 606/130 |
| 2003/0028147 A1 | 2/2003 | Aves et al. | |
| 2003/0093117 A1 | 5/2003 | Saadat | |
| 2003/0167031 A1 | 9/2003 | Odland | |
| 2003/0171738 A1 | 9/2003 | Konieczynski et al. | |
| 2004/0220606 A1 | 11/2004 | Goshgarian | |
| 2004/0243145 A1 | 12/2004 | Bobo, Sr. et al. | |
| 2005/0002918 A1 | 1/2005 | Strauss et al. | |
| 2005/0069495 A1 | 3/2005 | Baranowska-Kortylewicz et al. | |
| 2005/0085715 A1 | 4/2005 | Dukesherer et al. | |
| 2005/0101823 A1 | 5/2005 | Linares et al. | |
| 2005/0107738 A1 | 5/2005 | Slater et al. | |
| 2005/0245858 A1 | 11/2005 | Miesel et al. | |
| 2006/0121085 A1 | 6/2006 | Warren et al. | |
| 2006/0206150 A1 | 9/2006 | Demarais et al. | |
| 2007/0038181 A1 * | 2/2007 | Melamud et al. | 604/158 |
| 2008/0177183 A1 * | 7/2008 | Courtney et al. | 600/463 |
| 2010/0233081 A1 | 9/2010 | Warren et al. | |
| 2010/0280494 A1 | 11/2010 | Matsuura et al. | |
| 2011/0135569 A1 | 6/2011 | Dalke et al. | |

FOREIGN PATENT DOCUMENTS

| | | |
|---|---|---|
| WO | WO-99/30561 A1 | 6/1999 |
| WO | WO-2008/006040 A1 | 1/2008 |
| WO | WO-2008/020931 A2 | 2/2008 |
| WO | WO-2008020967 A2 | 2/2008 |
| WO | WO-2008020967 A3 | 2/2008 |
| WO | WO-2008/115566 A3 | 9/2008 |
| WO | WO-2008115511 A1 | 9/2008 |
| WO | WO-2008115566 A2 | 9/2008 |
| WO | WO-2008140808 A1 | 11/2008 |

OTHER PUBLICATIONS

International Application Serial No. PCT/US2008/003582, Written Opinion mailed Jul. 2, 2008, 5 pgs.

International Application Serial No. PCT/US2008/006040, International Search Report and Written Opinion mailed Aug. 6, 2008, 12 pgs.

International Application Serial No. PCT/US2008/03711, Search Report mailed Jul. 28, 2008, 6 pgs.

International Application Serial No. PCT/US2008/03711, Written Opinion mailed Jul. 28, 2008, 11 pgs.

International Application Serial No. PCT/US2007/016701, International Search Report and Written Opinion mailed Sep. 16, 2008, 9 pgs.

Aft, R. L, et al., "Enhancing targeted radiotherapy by copper(II)diacetyl-bis(N4-methylthiosemicarbazone) using 2-deoxy-D-glucose,", *Cancer Res.*, 63(17), (Sep. 1, 2003), 5496-504.

Bloomer, W. F, et al., "Letter: Antineoplastic effect of iodine-125-labelled iododeoxyuridine.", *Int J Radiat Biol Relat Stud Phys Chem Med.*, 27(5), (May 1975), 509-11.

Bobo, R. H, et al., "Convection-enhanced delivery of macromolecules in the brain.", *Proc Natl Acad Sci USA.*, 91(6) (Mar. 15, 1994), 2076-80.

Hall, W. A., et al., "Convection-enhanced delivery in clinical trials.", *Neurosurg Focus.*, 14(2), (Feb. 15, 2003), 1-4 (e2).

Hochberg, F. H., et al., "Assumptions in the radiotherapy of glioblastoma.", *Neurology*, 30(9), (Sep. 1980), 907-11.

Mischel, Paul S, et al., "DNA-microarray analysis of brain cancer: molecular classification for therapy.", *Nat Rev Neurosci.*, 5(10), (Oct. 2004), 782-92.

Mulford, D. A, et al., "The promise of targeted {alpha}-particle therapy.", *J Nucl Med.*, 46 (Suppl 1), (Jan. 2005), 199S-204S.

Ohgaki, Hiroko, et al., "Genetic pathways to glioblastoma: a population-based study.", *Cancer Res.*, 64(19), (Oct. 1, 2004), 6892-9.

Phillips, Heidi S, et al., "Molecular subclasses of high-grade glioma predict prognosis, delineate a pattern of disease progression, and resemble stages in neurogenesis.", *Cancer Cell.*, 9(3), (Mar. 2006), 157-73.

Raghavan, Raghu, et al., "Convection-enhanced delivery of therapeutics for brain disease, and its optimization.", *Neurosurg Focus*, 20(4), (Apr. 15, 2006), E12.

Vijayakumar, S, et al., "Advances in Radiation Oncology", *Lancet*, 349 (suppl II), (May 1997), 1-3.

Westphal, Manfred, et al., "A phase 3 trial of local chemotherapy with biodegradable carmustine (BCNU) wafers (Gliadel wafers) in patients with primary malignant glioma.", *Neuro Oncol.*, 5(2), (Apr. 2003), 79-88.

Yanik, G. A, et al., "Pilot study of iodine-131-metaiodobenzylguanidine in combination with myeloablative chemotherapy and autologous stem-cell support for the treatment of neuroblastoma.", *J Clin Oncol.*, 20(8), (Apr. 15, 2002), 2142-9.

U.S. Appl. No. 12/375,583, Final Office Action mailed Mar. 22, 2013, 24 pgs.

U.S. Appl. No. 12/531,325, Response filed Apr. 18, 2013 to Non Final Office Action mailed Nov. 20, 2012, 30 pgs.

European Application Serial No. 08727048.4, Extended European Search Report mailed Mar. 26, 2013, 6 pgs.

International Application Serial No. PCT/US2007/016701, International Preliminary Report on Patentability mailed Feb. 19, 2009, 5 pgs.

International Application Serial No. PCT/US2008/003582, International Preliminary Report on Patentability mailed Oct. 1, 2009, 7 pgs.

International Application Serial No. PCT/US2008/03711, International Preliminary Report on Patentability mailed Nov. 19, 2009, 12 pgs.

"Anthem Medical Policy: Convection Enhanced Delivery of Therapeutic Agents to the Brain", Policy No. SURG.00099, last review date Feb. 16, 2012, current effective date Apr. 11, 2012; Copyright CPT Only—American Medical Association [downloaded on Jan. 17, 2013 from http://www.anthem.com/medicalpolicies/policies/mp_pw_a053521.htm], (Feb. 16, 2012), 4 pgs.

U.S. Appl. No. 12/375,583, Non Final Office Action mailed Sep. 17, 2012, 20 pgs.

U.S. Appl. No. 12/375,583, Response filed Dec. 14, 2012 to Non Final Office Action mailed Sep. 17, 2012, 28 pgs.

U.S. Appl. No. 12/531,825, Response filed Jan. 23, 2013 to Non Final Office Action mailed Nov. 20, 2012, 20 pgs.

U.S. Appl. No. 12/531,825, Advisory Action mailed Feb. 11, 2013, 5 pgs.

U.S. Appl. No. 12/531,825, Final Office Action mailed Nov. 20, 2012, 14 pgs.

U.S. Appl. No. 12/531,825, Non Final Office Action mailed Mar. 27, 2012, 24 pgs.

U.S. Appl. No. 12/531,825, Response filed Jul. 26, 2012 to Non Final Office Action mailed Mar. 27, 2012, 24 pgs.

U.S. Appl. No. 12/599,564, Response filed Jan. 4, 2013 to Advisory Action mailed Dec. 5, 2012, 21 pgs.

U.S. Appl. No. 12/599,594, Response filed Nov. 29, 2012 to Final Office Action mailed Oct. 4, 2012, 32 pgs.

U.S. Appl. No. 12/599,594, Advisory Action mailed Dec. 5, 2012, 3 pgs.

U.S. Appl. No. 12/599,594, Examiner Interview Summary mailed Dec. 28, 2012, 3 pgs.

(56) References Cited

OTHER PUBLICATIONS

U.S. Appl. No. 12/599,594, filed Nov. 10, 2009, 105 pgs.
U.S. Appl. No. 12/599,594, Final Office Action mailed Oct. 4, 2012, 21 pgs.
U.S. Appl. No. 12/599,594, Non Final Office Action mailed May 3, 2012, 19 pgs.
U.S. Appl. No. 12/599,594, Notice of Allowance mailed Feb. 19, 2013, 8 pgs.
U.S. Appl. No. 12/599,594, Response filed Aug. 29, 2012 to Non Final Office Action mailed May 3, 2012, 27 pgs.
U.S. Appl. No. 12/599,594, Restriction Requirement mailed Oct. 27, 2011, 10 pgs.
"BlueCross BlueShield of Kansas City: Convection-Enhanced Delivery of Therapeutic Agents to the Brain", Policy No. 8.01.504, originated Mar. 2007, last review Mar. 2012; BlueCross BlueShield of Kansas City, (Mar. 2007), 6 pgs.
"Cigna Medical Coverage Policy: Convection-Enhanced Delivery of Therapeutic Agents to the Brain", Cigna Coverage Policy No. 0476, effective date Apr. 15, 2012; Cigna Corporation, (Apr. 15, 2012), 5 pgs.
Bogdahn, U., et al., "Targeted therapy for high-grade glioma with the TGF-β2 inhibitor trabedersen: results of a randomized and controlled phase IIb study", Neuro Oncol., 13(1), (Jan. 2011), 132-42.
Buchegger, Franz, et al., "Highly Efficient DNA Incorporation of Intratumourally Injected [125I]Iododeoxyuridine Under Thymidine Synthesis Blocking in Human Glioblastoma Xenografts", Int. J. Cancer: 110, (2004), 145-149.
Ferguson, S., et al., "Convection enhanced drug delivery of novel therapeutic agents to malignant brain tumors", Curr Drug Deliv., 4(2), (Apr. 2007), 169-80.
Ferguson, S. D, et al., "Convection-enhanced delivery for treatment of brain tumors", Expert Rev Anticancer Ther., 7(12 Suppl), (Dec. 2007), S79-85.
Hall, Walter A., et al., "Convection-enhanced delivery in clinical trials", Neurosurg Focus 14(2):Article 2, 2003, (Feb. 2003), 1-4.
Kunwar, S., et al., "Phase III randomized trial of CED of IL13-PE38QQR vs Gliadel wafers for recurrent glioblastoma", Neuro Oncol., 12(8), (Aug. 2010), 871-81.
Laske, D. W, et al., "Tumor regression with regional distribution of the targeted toxin TF-CRM107 in patients with malignant brain tumors", Nat Med., 3(12), (Dec. 1997), 1362-8.
Lopez, K. A, et al., "Convection-enhanced delivery in the treatment of malignant glioma", Neurol Res., 28(5), (Jul. 2006), 542-8.
Neshasteh-Riz, A, et al., "Incorporation of Idodeoxyuridine in Multicellular Glioma Spheroids: Implications for DNA-Targeted Radiotherapy Using Auger Electron Emitters", British Journal of Cancer, (1997), 493-499.
Patel, S. J, et al., "Safety and feasibility of convection-enhanced delivery of Cotara for the treatment of malignant glioma: initial experience in 51 patients", Neurosurgery, 56(6), (Jun. 2005), 1243-52; discussion 1252-3.
Reza, M. S, et al., "Iodo-2'-Deoxyuridine (IUdR) and 125IUdR Loaded Biodegradable Microspheres for Controlled Delivery to the Brain", J. Microencapsul, vol. 15, (1998), 789-801.
Sampson, J. H, et al., "Poor drug distribution as a possible explanation for the results of the PRECISE trial", J Neurosurg., 113(2), (Aug. 2010), 301-9.

\* cited by examiner

GUIDANCE AND IMPLANTATION OF CATHETERS

CLAIM OF PRIORITY TO RELATED APPLICATIONS

This application is a U.S. National Stage Filing under 35 U.S.C. 371 from International Patent Application Serial No. PCT/US2008/003711, filed on Mar. 20, 2008, and published on Sep. 25, 2008 as WO 2008/115566, which claims the priority of U.S. Provisional Patent Application Ser. No. 60/895,916, filed on Mar. 20, 2007, and U.S. Provisional Patent Application Ser. No. 60/917,226, filed on May 10, 2007, which applications and publication are incorporated herein by reference in their entirety.

BACKGROUND OF INVENTION

In the treatment of neoplasia, such as solid tumors in the early stages, surgical excision or ablation with radiation often provides a successful form of therapy. However, this is not the case for many solid tumors that have advanced to later stages. Locally advanced or locally invasive solid tumors are primary cancers that have extensively invaded or infiltrated into the otherwise healthy tissues surrounding the site where the tumor originated. Locally advanced tumors may arise in tissues throughout the body, but unlike early stage tumors may not be amenable to complete surgical excision or complete ablation using radiation treatments. Due to the invasion of the surrounding tissues by tumor processes, any surgical procedure that would serve to remove all the cancerous cells would also be likely to maim or destroy the organ in which the cancer originated. Similarly, radiation treatments intended to eradicate the cancerous cells left behind following surgery frequently lead to severe and irreparable damage to the tissues in and around the intended treatment field. Often, surgery is combined with radiotherapy, chemotherapy or a combination of adjuvant therapies designed to eliminate the malignant cells that could not be removed by the surgery. However, when a tumor has infiltrated into otherwise healthy tissues surrounding the site where the tumor originated, even combination treatments including surgery plus radiation therapy, or surgery plus radiation therapy plus chemotherapy may not be capable of eradicating the tumor cells without causing severe damage to the tissues in the treatment field. Neither surgeons nor radiotherapists have the tools to eliminate individual tumor cells, microscopic tumor processes, or tumor-associated vasculature from the otherwise normal tissue surrounding locally advanced solid tumors. Nevertheless, in the interest of preserving the overall structure of tissues being invaded by cancer cells, conventional radiation therapy is widely used in the treatment of locally advanced solid tumors.

Conventional radiation therapy involves the exposure of cancerous tissues to megavoltage x-ray beams (i.e. gamma photons) and is a well-established anti-cancer treatment modality. Conventional radiation therapy is curative for selected early stage tumors, and is the treatment of choice to mitigate the symptoms of locally advanced solid tumors and selected metastatic tumors. Conventional radiation therapy can be administered using quantitative and reproducible treatment protocols, and x-rays are synergistic when administered with certain cytotoxic drugs and biological agents. Conventional radiation therapy is an effective anticancer treatment that is used to treat tumors throughout the body.

Despite the above mentioned benefits, and its widespread use, conventional radiation therapy cannot cure locally advanced solid tumors, because, in order to gain access to a tumor mass, x-ray beams usually must pass completely through the body; therefore, exposure to normal tissues is inevitable. In addition, x-ray beams lack the microscopic accuracy needed to eliminate individual cancer cells from the treatment field. X-rays cannot eradicate or cure most types of locally advanced solid tumors, because they lack the specificity needed to kill cancer cells while sparing the normal cells in the treatment field.

Notwithstanding the macroscopic scale of x-ray beams, the increased accuracy of radiotherapy beams is recognized to improve the clinical benefit-to-risk ratio. Indeed, digital imaging technologies are used to help radiotherapists with pre-treatment planning. For example, CT and MRI are used to map the 3-D contours of solid tumors, and thereby define a "treatment field" to be irradiated with x-rays. The goal is to irradiate tumors with a wide variety of 3-D shapes while avoiding the tissues surrounding the treatment field. Unfortunately, this approach is of limited value even in instances when the x-ray beam can be focused precisely on the treatment field. The main problem is that x-rays cannot discriminate between the cancer cells and normal cells within the treatment field. Because of this conventional radiation is associated with side effects, often severe, including mucositis, alopecia, dermatitis, proctitis, enteritis, and tissue necrosis. Brain tissue is particularly sensitive to the toxic effects of ionizing radiation. Radiotoxic effects in the CNS include cognitive impairments, inflammation of the white matter and full blown inflammatory brain necrosis.

Regardless of how precisely one defines the treatment field, and regardless of how precisely the x-ray beam is projected through the treatment field, x-rays will damage normal cells in the treatment field, and radiotherapy beams do not have the microscopic accuracy needed to eliminate individual cancer cells from the treatment field. Thus, even the most precise digital pre-treatment planning cannot overcome the inherent deficiencies of ionizing radiation.

Even using a combination of systemic agents and conventional radiation, nearly one third of patients with locally advanced solid tumors relapse (Vijaykumar, S. and Hellman, S., "Advances in Radiation Oncology," Lancet, 349[S11]: 1-3 (1997)). Most types of chemotherapy also suffer from a lack of tumor specificity and also cause collateral damage to normal tissues, since chemotherapeutic agents are distributed throughout the body and exert their effects on normal cells as well as malignant cells. Many systemic chemotherapy agents act on cells undergoing DNA synthesis and cell division, and thus may impact many cell populations throughout the body in addition to the target cancer cells.

The deficiencies of current treatment modalities are especially glaring with respect to specific types of cancer, for example glioblastoma multiforme (GBM), a highly aggressive type of cancer that constitutes the most common form of brain malignancy. Indeed, after nearly 35 years of investigations involving hundreds of experimental treatments and thousands of GBM patients participating in clinical trials, the prognosis of patients with newly diagnosed GBM is dismal. In a recent survey, the survival following the diagnosis of GBM is only 42% at 6 months, 18% at one year, and 3% at 2 years (Ohgaki, et al., "Genetic pathways to glioblastoma: A population-based study," Cancer Research, 64:6892-6899 (2004)).

The currently favored treatment for newly diagnosed GBM is surgical resection followed by a course of ionizing radiation plus oral temozolomide, a chemotherapy agent that is administered during and after the course of radiation. In patients receiving this treatment, the best currently available, the median prolongation pf survival is only about 2-3 months beyond surgery and radiation alone.

Recently, techniques have been developed to increase the effective concentration of chemotherapeutic agents at a tumor site. In the treatment of GBM, interstitial or localized chemotherapy has been used with modest success. Wafers containing carmustine (a chemotherapy agent) are inserted into the cavity created by surgical removal of the tumor. The wafers release carmustine into the brain tissue in the immediate vicinity of the brain tumor. This treatment has been shown to increase the median survival from 11.6 months to 13.9 months in patients also treated with surgery and radiation beam therapy (Westphal, M., et al., "A phase III trial of local chemotherapy with biodegradable carmustine (BCNU) wafers in patients with primary malignant glioma," *Neuro-oncology,* 5:79-88 (2003)). Interstitial treatments may be particularly well suited for treatment of GBM, as greater than 90% of GBM tumors that recur following surgical resection are localized within 2 cm of the surgical margin (Hochberg, F. H., and Pruitt, A., *Neurology,* 30:907-911 (1980)). Localizing the concentration of a chemotherapeutic agent by physical techniques (as distinct from biochemical targeting) seems to offer certain advantages compared to systemic chemotherapy. However, the challenge is great, because the majority of chemical entities do not diffuse far into brain tissue or other types of solid tissues.

Another development in physically localized delivery of anticancer agents is convection enhanced delivery. In this technique, a fluid is delivered directly to the cancerous tissues and not through the circulatory system. The fluid is applied under sustained pressure such that the liquid moves by the forces of bulk flow through the interstices of the tissue, carrying with it any dissolved materials. Convection enhanced delivery also bypasses the blood-brain barrier in brain tissue. For example, see Bobo, R. H., et al., "Convection-enhanced delivery of macromolecules in the brain," *Proc. Nat. Acad. Sci. USA,* 91: 2076-2080 (1994); Laske, D W. et al. "Convection-enhanced drug delivery," U.S. Pat. No. 5,720,720 (Feb. 24, 1998); Raghavan, R. et al., "Convection-Enhanced Delivery of Therapeutics for Brain Disease, and Its Optimization," *Neurosurgery Focus* 20(4):E12 (2006); and Hall, W. A., et. al,. "Convection-enhanced delivery in clinical trials," *Neurosurgery Focus* 14, 1-4, (2003). By comparison to diffusion-based local drug delivery, convection-enhanced delivery serves to increase the effective distance over which a bioactive agent can be delivered into solid tissues. Bulk flow or convection-enhancement of treatment fluid results from the application of a sustained pressure as needed to generate flow rates of at least 0.5 microliters per minute from each catheter tip implanted into the cerebral tissue. For example, see Bobo, R. H., et al., "Convection-enhanced delivery of macromolecules in the brain," *Proc. Nat. Acad. Sci. USA,* 91: 2076-2080 (1994); Laske, D W. et al. "Convection-enhanced drug delivery," U.S. Pat. No. 5,720,720 (Feb. 24, 1998); The flow rates required to generate bulk flow in various other tissues, such as specific types of cancerous tissues, have not been determined.

Convection enhanced delivery has been used with modest success to deliver a number of bioactive agents, mostly proteins, into cerebral tissues of patients with malignant brain tumors. Convection enhanced delivery usually involves 2-4 catheters that are inserted such that the catheter tips are located at selected positions in the vicinity of the surgical resection cavity. The catheters are often inserted one at a time and from multiple points of origin on the outer surface of the brain.

Currently available methods of convection enhanced delivery have several limitations and drawbacks. One of the biggest problems is to determine the optimal position of the catheter tips. This is important not only to ensure that the infusate gains access to the entire intended treatment field, but also to minimize exposure to uninvolved regions of the brain. Optimal catheter placement is especially challenging given the highly variable size and shape of surgical resection cavities. There is also substantial variation in the anatomy and fluid convection dynamics in the cerebral tissues, i.e. white matter tracts provide more rapid and linear convective flow than gray matter. Regional differences in anatomy and fluid dynamics increase the challenge of accurate catheter placement. Another problem that aggravates the optimal positioning of catheter tips is tissue swelling. Cerebral tissues tend to shift their position during the early postoperative period as tissue edema resolves. This makes it quite difficult to accurately position the tips of catheters into the perimeter of the surgical resection cavity. To address this issue, surgeons may wait up to a week after the initial brain tumor operation, when swelling has diminished, to insert the catheters.

Convection enhanced delivery, as currently applied to the treatment of human brain tumors, employs relatively thick catheters with at least a 2.5 mm outer diameter. Such catheters provide relatively low resistance to backflow around the outer wall of the catheter as compared to smaller catheters. Thick catheters must be advanced at least a couple of centimeters into the cerebral tissue in order to provide an adequate seal needed to stop or minimize backflow. This requirement has prompted surgeons to insert such catheters from multiple points on the surface of the brain. The surgeon may inserts such catheters from points of entry within the sulci, i.e. the gaps between the spaghetti-like gyri on the surface of the brain. Insertion of such thick catheters from inside of the surgical resection cavity is challenging because of the minimum depth requirement, by their limited pliability, and by their sheer bulk. The use of 2.5 mm OD catheters may increase the risk of hemorrhage and/or trauma to nervous tissues as compared with thinner catheters. Given the above constraints it is very difficult to consistently arrange the tips of thick catheters into an orderly distribution around many surgical resection cavities.

Another limiting factor is that each catheter supplies a large proportion of the intended treatment field, e.g. 33% of the treatment field for 3 catheters, and 50% of the treatment field for 2 catheters. A high proportional flow per catheter is an unavoidable consequence of using only a few catheters, and has the effect of reducing the accuracy of convection enhanced delivery. Suboptimal placement of a single catheter tip can markedly affect the overall pattern of biodistribution. In addition, the use of a high fractional flow per catheter, and the fact that the catheters must be inserted from the surface of the brain, limits the surgeon's available options for catheter insertion.

Based upon clinical experience from many convection enhanced delivery studies involving patients with brain tumors, 2-3 catheters appear to be insufficient to provide optimal biodistribution of drugs around many surgical resection cavities.

The effective treatment of locally advanced solid tumors, including GBM, requires not only improved methods of drug delivery, but also therapeutic agents capable of eliminating the cancer cells while at the same time sparing normal tissues that have been invaded by the cancer cells. In this regard, a major issue revealed by studies of gene expression profiling, is that tumors are genetically and metabolically much more heterogeneous than previously anticipated. Tumors may be genetically and metabolically heterogeneous despite a common organ or tissue of origin, and despite a very similar appearance under the microscope. This is especially true of GBM and other malignant gliomas that arise in the central nervous system. For example, see H. S. Phillips et al., "Molecular subclasses of high-grade glioma predict prognosis, delineate a pattern of disease progression, and resemble stages in neurogenesis," Cancer Cell 9, 157-173 [2006]; and P.S. Mischel et al., "DNA-Microarray Analysis of Brain Cancer: Molecular Classification for Therapy," *Nature Cancer Reviews*, 5:782-792 (2004). In view of the tumor heterogeneity, biochemical targeting, i.e. the search for agents that specifically target each tumor type, is a daunting challenge.

New and effective treatments are needed to eliminate tumor cells with a wide range of genetic and metabolic profiles; to eliminate tumor stem cells, which have the capacity for self-renewal, unlimited proliferative potential, and an inherent resistance to chemotherapy and ionizing radiation; and to minimize or avoid toxicity to normal cells and tissues both inside and outside of the treatment field. One approach to this problem is physically localized delivery of an agent capable of killing many different types of cancer cells, while at the same time having minimal or no toxicity to normal cells within the treatment field. This approach is distinct from the concept of targeted therapy, in which a different drug mechanism may be needed to treat each tumor according to its distinct genetic and metabolic profile.

A unique cell killing mechanism that has garnered considerable interest is the release of Auger electrons. These electrons are emitted by radionuclides that decay by electron capture and internal conversion. Examples of Auger emitting radionuclides include $^{123}$Iodine, $^{125}$Iodine, $^{77}$Bromine and $^{80m}$Bromine. Auger electrons have energies even lower than the energy of the beta particle emitted by tritium. This effect is amplified, because some Auger emitters release multiple electrons with each nuclear transformation. The low energy of the Auger electrons results in extremely short particle path lengths within tissues, which is highly desirable, because it minimizes collateral damage.

One molecular entity incorporating $^{125}$I is [$^{125}$I]-iodouridine-deoxyriboside ($^{125}$IUDR), a thymidine analogue. $^{125}$IUDR is recognized by DNA polymerases as thymidine, and thus is incorporated into the chromosomes at times of DNA synthesis. Once incorporated into the DNA, the Auger electrons, with their very short range, have access to the chemical backbone of the DNA double helix. When the $^{125}$I atom disintegrates, Auger electrons cause irreparable destruction of the chromosomes within the target cell, but with minimal effect on cells in the immediate vicinity of the target cell. $^{125}$IUDR and related compounds destroy cells that make DNA, but have little or no effect on other cells.

Despite the recognition that $^{125}$IUDR has a unique cell killing capability, and despite many years of research aimed at exploiting this mechanism of action, including the concept of directly introducing $^{125}$IUDR into tumors (for example, see Kassis et. al., "Treatment of tumors with 5-radioiodo-2'-deoxyuridine," U.S. Pat. No. 5,077,034), these agents have not been successfully applied to the treatment of cancer. The delivery of $^{125}$IUDR and related agents to solid tumors, using systemic or local administration, has proven to be extremely challenging.

There is a need for new devices and methods of use aimed at exploiting the unique mechanism of action of $^{125}$IUDR, $^{123}$IUDR and related compounds. New approaches are needed to deliver $^{125}$IUDR (and other compounds) to solid tumors with the intent to eliminate cycling tumor cells, including the tumor-maintaining stem cells and their progenitors, while at the same time sparing normal tissues that have been invaded by the cancer cells. This need includes methods for delivery of such agents directly into the tumors and into the normal tissues that have been invaded by tumor cells, particularly in away that provides for substantially uniform treatment of an often-irregularly shaped volume of tissue.

SUMMARY

The present invention is directed to systems and methods for delivery of bioactive agents, such as anticancer agents, to target tissues, for example cancerous tissues, for example tissues disposed in the brain, head or neck tissues, esophagus, intestines, pancreas, bladder, prostate gland, ovary, colon, or rectum of a patient. Various embodiments of the invention provide a catheter system for delivery of a pressurized liquid solution or suspension containing a bioactive agent via a spatially defined catheter implantation into a targeted body tissue of a patient; the system comprising: a biocompatible catheter or a plurality thereof, each catheter being hollow, and linear, curvilinear, or helical; each catheter being adapted for insertion into the body tissue and for delivery of the solution or suspension of the bioactive agent through the catheter into the tissue; and the catheter system being adapted for guiding emplacement of each of the catheters into the tissue to form the spatially defined catheter implantation; wherein each catheter is emplaced within the tissue individually, in subsets, or all concurrently, to provide the spatially defined implantation such that the pressurized solution or suspension of the bioactive agent is delivered through each catheter to a volume of target tissue.

Various embodiments provide a catheter guide structure comprising catheter guide tubes or passageways.

Various embodiments of the invention provide an electronic, radiofrequency, ultrasound, or video-assisted computerized digital tissue navigation system adapted for guiding the emplacement of the catheters to form the spatially defined implantation within the targeted body tissue. The digital navigation system can make use of digitized tissue or organ maps to guide the emplacement of the catheters. The tissue or organ maps can be pre-treatment maps from the patient being treated, can be maps obtained from the patient during the course of treatment as the tumor dimensions change, or can be general anatomical maps as are well known in the art.

Various embodiments of the invention provide a pressurized liquid supply system adapted for delivery of a liquid via a manifold to each of the plurality of catheters; wherein the liquid supply system comprises a pressurizer adapted to apply a pressure to the liquid solution and a manifold to deliver the liquid under pressure to each of the plurality of catheters such that the liquid can pass through each catheter into the targeted body tissue.

Various embodiments of the invention provide the catheters and the catheter system comprising a catheter guide device comprising catheter guide tubes wherein at least some of the catheter guide tubes comprise a memory material such that a tube comprising the memory material is adapted to assume a predetermined arc upon insertion into tissue or into a position adjacent to the tissue for insertion of the catheter into the tissue. The catheter guide tubes can each contain a single respective catheter or can contain multiple catheters. Each guide tube can be linear, curvilinear, or helical, and can be bifurcated or unbifurcated. When bifurcated, each tube can guide each of a pair of catheters to different points within the tissue for emplacement.

In various embodiments, the plurality of catheters and the catheter guide device can be adapted to remain connected after the catheters have been emplaced within the tissue to provide an anchoring effect. For example, one subset of catheters can be emplaced within the tissue at an angle other than orthogonal to the guide structure and a second subset can be emplaced at another angle other than orthogonal to the guide structure, for example in a splayed fashion, to provide an anchoring effect.

In various embodiments the tissue navigation system includes a probe adapted to be placed adjacent to the targeted body tissue or within the targeted body tissue to inform the tissue navigation system by transmission of electronic, radiofrequency, ultrasound, or video data to the tissue navigation system such that the tissue navigation system provides information directing emplacement of the catheters. The probe can include a fiberoptic video system to relay visual information. Of the probe can include an ultrasonic transponder to provide spatial information about the tissue structure. The visual information or ultrasound image can be used to direct or guide emplacement of the catheters, optionally in conjunction with a tissue or organ map.

In various embodiments, the probe is further adapted to provide surgical functions to assist in emplacement of the catheters. The probe can include scissor, straight blade, rotary blade, cutting laser, or electrocautery tools, or a combination thereof. The probe can be adapted to be steered or directed within a patient's body from the exterior of the body. The tissue navigation system can be adapted to steer or direct the probe within the patient's body.

Various embodiments provide a catheter guide device including a tile or tiles, wherein the tile comprises one or more catheter guide passageways therethrough adapted to position and steer the catheter into position within the tissue and the tile further comprises a probe opening therethrough adapted to removably hold the probe in close proximity to a point of entry of the catheter into the tissue. The tiles can also include probe openings to position the probe immediately adjacent to the catheter guide to inform the emplacement of the catheter within the tissue. A plurality of tiles can be disposed on and connected to a mesh, the mesh being adapted to be laid on a surface, such as the surface of a body organ, to define multiple points of emplacement of each of the plurality of catheters.

In various embodiments the bioactive agent can include Auger-electron emitting radionucleoside or an analog or a prodrug thereof, such as a halogenated nucleoside analog, for example 5-[$^{123}$I]-iodouridine 2'-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine 2'-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine 2'-deoxyribonucleoside, 8-[$^{125}$I]-iodoadenine 2'-deoxyribonucleoside, 5-[$^{77}$Br]-bromoadenine 2'-deoxyribonucleoside, 5-[$^{80m}$Br]-bromoadenine 2'-deoxyribonucleoside or 5-[$^{211}$At]-astatouridine 2'-deoxyribonucleoside. In various embodiments the bioactive agent can include an Auger-electron emitting nucleoside prodrug, such as a 3'- or 5'-phosphate or carboxylate ester of a deoxyribosyl or ribosyl moiety of the radionucleoside. In various embodiments, the bioactive agent can include a second medicament, such as an anticancer drug, an antiinflammatory drug, or an antibiotic.

Various embodiments of the invention provide a method of using the inventive catheter system for emplacement of a spatially defined catheter implantation adapted for delivery of a pressurized liquid containing a bioactive agent to a volume of body tissue, the method comprising with the catheter system directing the emplacement of the catheter or each of the plurality of catheters into the body tissue such that the spatially defined catheter implantation is provided; then, connecting a source of a pressurized liquid containing a solution or suspension of the bioactive agent to each of the plurality of catheters, then delivering the liquid under pressure from the source to each of the catheters, such that the liquid containing the bioactive agent passes through the catheters under pressure into the body tissue. The delivery of the bioactive agent to the tissue can be medically indicated for treatment of a malcondition of the tissue. The malcondition can be a cancer, such as a locally advanced solid tumor. The cancer can be a cancer of brain, head or neck, esophagus, prostate, ovary, liver, pancreas, bladder, colon, or rectum.

An embodiment of the inventive method can include the administration of the solution of the bioactive agent at a variety of pressures, flow rates, and durations of administration. For example, the solution can be administered continuously, intermittently, at various rates, and for various periods of time. An embodiment of the inventive method can include the administration of the solution of the bioactive agent under pressure such that bulk flow is created in the target tissues, i.e. by convection-enhanced delivery.

An embodiment of the present invention is also directed to a method of treating a patient for a malcondition wherein intra-tissue delivery of a bioactive agent is medically indicated, using the inventive catheter system, by positioning a catheter guide device within or adjacent to the target tissue of the patient such that the guide device is adjacent to tissues targeted for the intra-tissue delivery of the bioactive agent; then, with or without the addition of a computerized, digital, electronic, ultrasound or video-assisted navigation component, inserting a plurality of catheters, either as a pre-formed array, or through a catheter guide system such that the catheters are directed by passageways to form a spatially defined catheter implantation; and connecting the liquid supply system to the base portion of each catheter, either individually or through a manifold, such that pressurized liquid can be delivered through the catheter to the target tissue; and then supplying a liquid comprising a solution of the bioactive agent from the liquid supply system through a plurality of catheters into the target tissue by way of the ports.

In various embodiments bioactive agent is a radiological agent, which can be an Auger electron emitting isotope, for example $^{123}$I or $^{125}$I, which causes mostly short-range damage to cells in which it is disposed, thus limiting undesired radiation damage to non-malignant cells. The Auger electron emitting isotope can be part of a molecule adapted to be incorporated into the cellular structure of cancerous cells in the target tissue; for example, a nucleoside or nucleotide analogue can be radiolabeled to provide a bioactive structure suitable for use in the inventive method. $^{125}$I-iodouridinedeoxyriboside (IUDR) is an example.

In various embodiments the pressurized liquid flows through each of the plurality of catheters at a substantially equal rate. In various embodiments the pressurized liquid flows through a first subset of the plurality of catheters at a different rate than the rate at which the liquid flows through a second subset of the plurality of catheters. For example, the first subset of catheters and the second subset of catheters can be adapted to control the respective flow rates therethrough to provide a relative differential flow rate between the first subset and the second subset.

BRIEF DESCRIPTIONS OF THE DRAWINGS

FIG. 1 depicts a catheter guide device of the invention with memory metal or memory polymer guide tubes.

FIG. 2A is a side view of a four-catheter guide device that uses memory metal or memory polymer preformed guide tubes to determine the direction and location of catheter tip insertion into tissue with one catheter per tube, prior to extension of the memory material guide tube from a bundle within the sleeve; FIG. 2B shows the tubes extended into the tissue or into a position adjacent to the tissue for insertion of the catheter into the tissue from the sleeve to guide catheter emplacement; FIG. 2C shows a guide device having a guide sleeve with eight guide tubes and their respective catheters.

FIGS. 7A, 7B, and 7C depict a guide device adapted to insert catheters into tissue at angles that provide anchoring of the catheters and device.

FIGS. 8A, 8B, and 8C depict a guide device to insert catheters into tissue at angles that provide anchoring of the catheters and device.

FIGS. 9A and 9B depict a guide device that can be used to anchor the catheters into tissue by slowly expanding the angle (A before, B after) between the catheter tips slowly while inserting the device into tissue.

FIGS. 10A-D depict a double "claw" design that is spring loaded to insert two sets of catheters into a target tissue.

FIGS. 11A-C depict a radiofrequency or other type of locating device adapted to be used with the navigation and stereotactic system of the invention to determine the location of a catheter within a body tissue.

Figure 1:
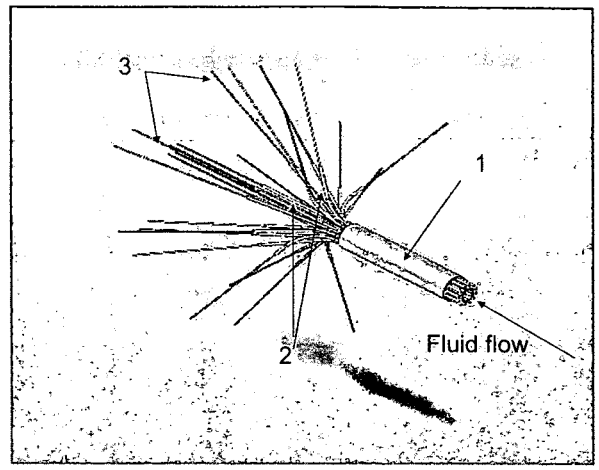

FIGS. 12A1-C1 and 12A2-C2 depict catheter placement devices that can be used with a radiofrequency locating device as described in the accompanying discussion.

FIGS. 13A-G depict catheter placement devices that can be used with a radiofrequency locating device as described in the accompanying discussion.

FIGS. 14A and 14B depict catheter placement devices attached to a radiofrequency locating device as described in the accompanying discussion.

FIGS. 15A and 15B show the use of the articulation of the radiofrequency locating device with a catheter insertion device as described in the accompanying discussion.

Figure 16A:
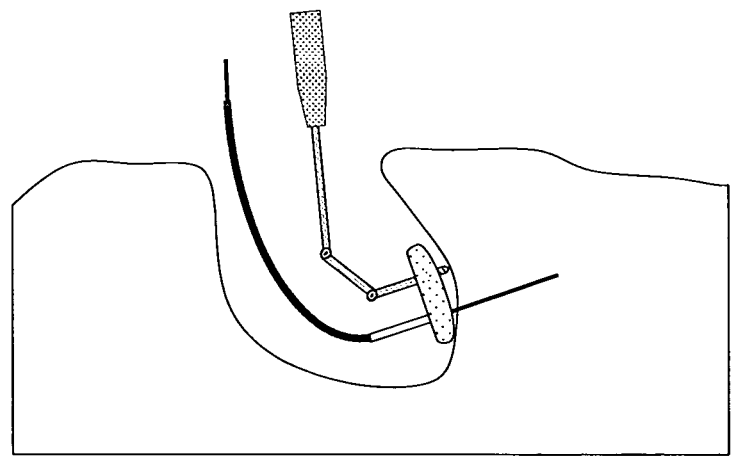

FIG. 16A shows the insertion of a catheter into the side of a body cavity, such as a brain tumor resection cavity, using the articulation of the device.

Figure 16B:
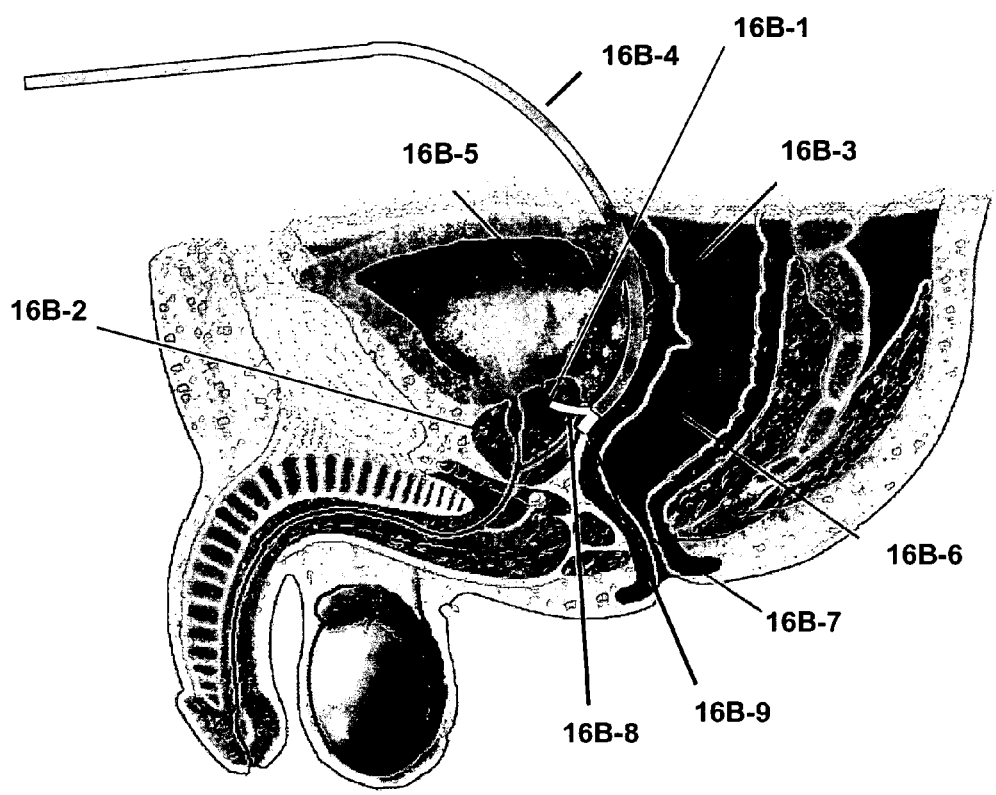

FIG. 16B shows the insertion of a catheter into the posterior lobe of the prostate gland, using a flexible video-assisted endoscope that has been advanced past the recto-vesical fascia between the bladder and rectum.

FIGS. 17A and 17B show alternate designs of tiles for single catheters using a radiofrequency probe to locate the site of catheter insertion.

FIGS. 18A-C show different forms of tiles that can be used to be implanted into a hemispherical tissue resection cavity.

Figure 19:
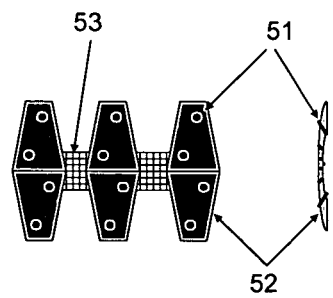

FIG. 19 shows a form of tile with an abbreviated top section.

FIGS. 20A-C show a form of tile with only the top half of the templates.

Figure 21:
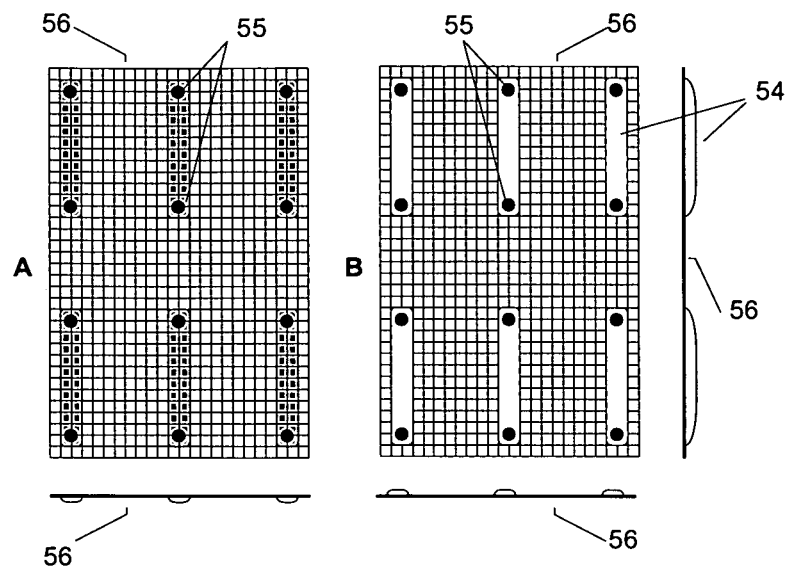

FIG. 21 depicts a form of the mesh mat guide device to facilitate catheter placement as described in the accompanying discussion.

Figure 22:
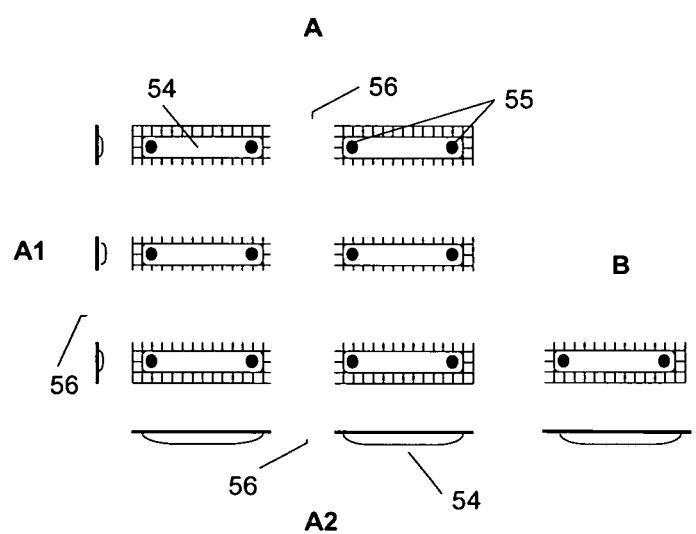

FIG. 22 depicts the device in FIG. 21 separated into any number of different devices with single or multiple placement devices attached to each other.

Figure 23:
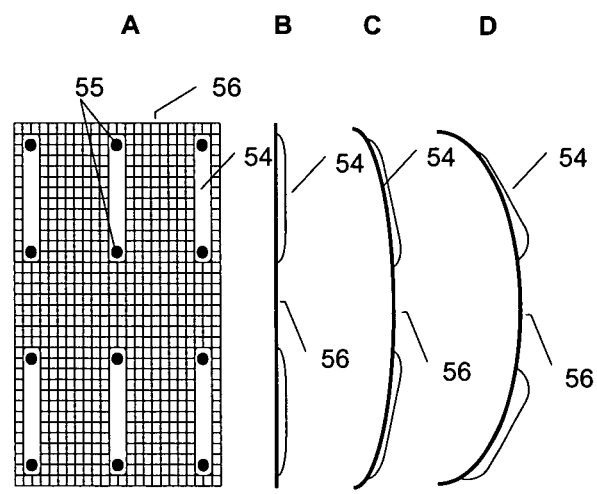

FIG. 23 shows that the mesh conforming to the surface of a tissue resection or other body cavity.

Figure 24:
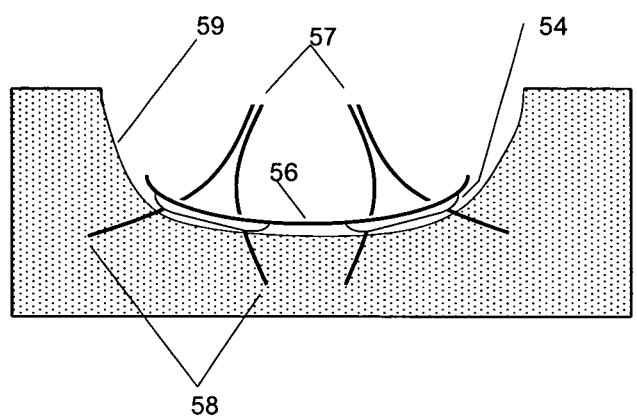

FIG. 24 shows the mesh conforming to the surface of a tissue resection or other body cavity.

Figure 25:
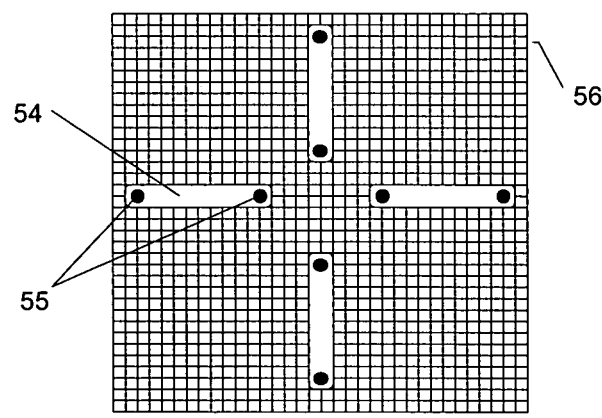

FIG. 25 shows another potential geometry for the mesh mat design of catheter placement devices.

Figure 26:
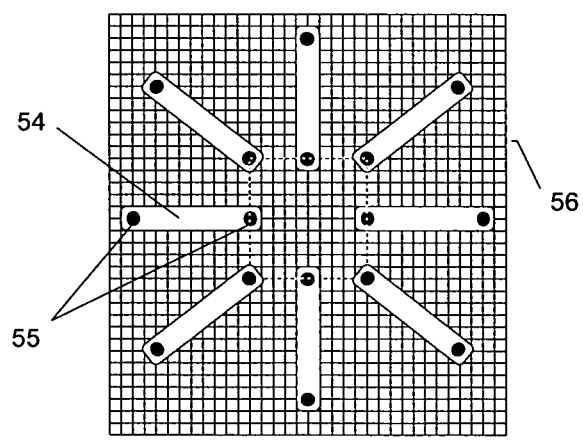

FIG. 26 shows another potential geometry for the mesh mat design of catheter placement devices.

Figure 27:
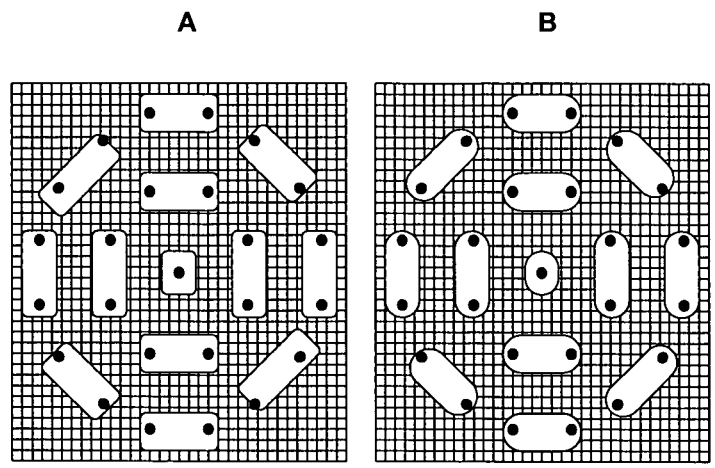

FIG. 27 shows another potential geometry for the mesh mat design of catheter placement devices.

Figure 28:
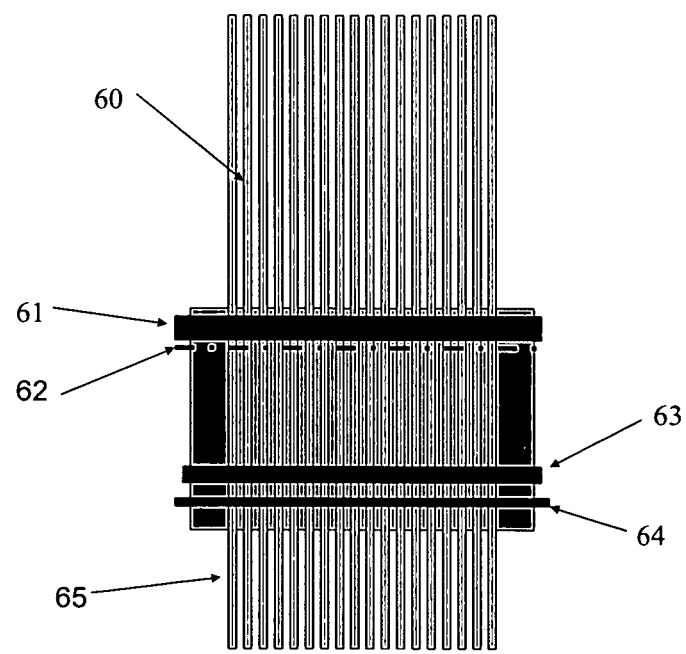

FIG. 28 depicts a catheter manifold device to aide in adjusting catheter length and connecting such catheters to the liquid supply system.

Figure 29:

FIG. 29 is a cross section of the device in FIG. 28.

Figure 30:
Figure 30:
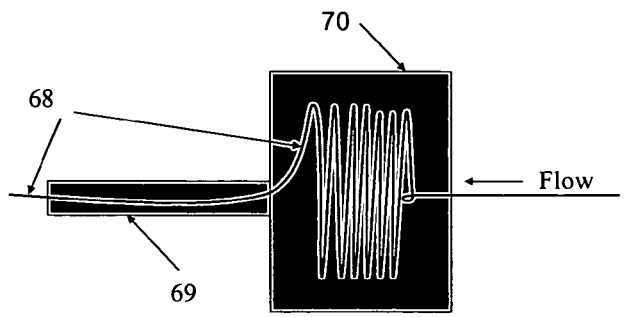

FIG. 30 shows a loop of excess catheter stored in a housing device.

Figure 31:
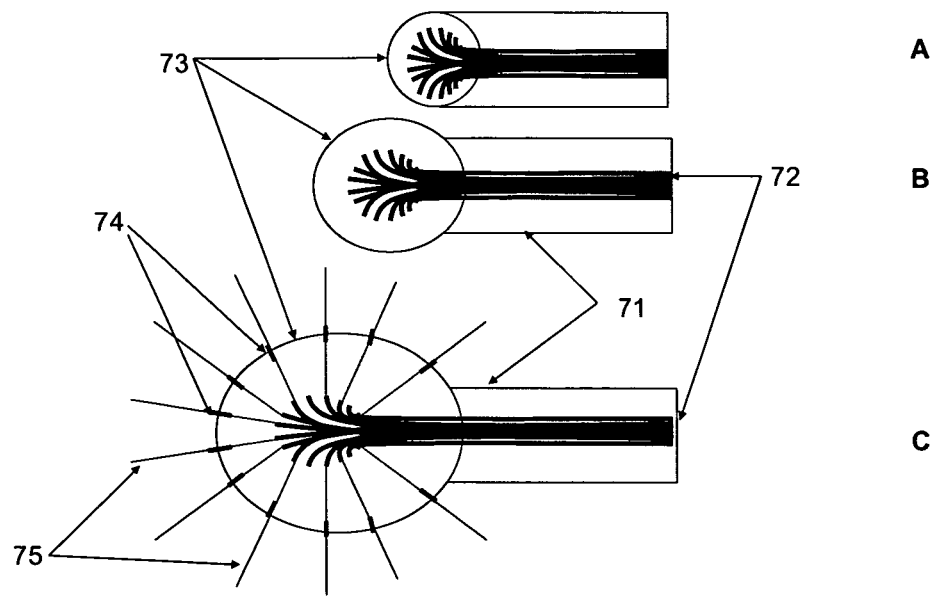

FIG. 31 shows an expandable catheter implantation device to fill spherical and irregularly shaped cavities and insert drug delivery catheters.

DETAILED DESCRIPTION OF THE INVENTION

The inventive catheter system enables the stereotactic emplacement of a plurality of catheters into a target tissue or field of treatment. The emplacement can be guided by an electronic, radiofrequency, ultrasound, or video-assisted computerized digital navigation and stereotactic system. The individual sources of bioactive agent or drug emanating from each catheter provides an overlapping field of treatment in the target tissue to expose the entire treatment field to an antineoplastic agent, radiopharmaceutical agent, or other pharmaceutical agent. The inventive catheter guidance and guidance system may be used to create essentially any 3-dimensional spatial array of catheters within the target tissue using a catheter guide template, comprising catheter guide tubes or passageways, or both, to guide the catheters into the spatially defined implantation in the target tissue or field of treatment.

Various embodiments of the present invention involve a catheter guide device comprising catheter guide tubes, passageways, or both, to implant a plurality of catheters, inserted either singly or in groups, into a target tissue of a patient to form a system for the delivery of a liquid solution of a bioactive agent into a volume of the target tissue of a patient. The system includes a biocompatible catheter or a plurality of biocompatible catheters, each catheter comprising a linear, curvilinear, or helical hollow tube adapted for insertion into the body tissue, for remaining within the tissue for a period of time, and for delivery of a pressurized solution or suspension of the bioactive agent through the tube into the tissue. The catheter system is adapted for emplacement of the plurality of catheters into a volume of tissue to form the spatially defined implantation of catheters within the tissue. Various embodiments of the invention include a pressurized liquid supply system adapted for delivery of a liquid via a tube or manifold to the catheters. Each catheter includes a distal portion for insertion into the tissue, and a base portion adapted for connection to the tube or manifold attached to the pressurized liquid supply system such that the pressurized liquid can pass through the hollow tube of each catheter into the tissue.

Various embodiments of the present invention include an electronic, radiofrequency, ultrasound or video-assisted computerized digital navigation and stereotactic system to guide the implantation of the plurality of catheters into the target tissue. The catheter guide device comprising catheter guideway passageways, catheter guideway tubes, or both, is controlled by the digital navigation and stereotactic system to guide movement of one or more catheters through the passageway or tube for insertion into the tissue, such that upon insertion of the catheters, the implantation thus formed has a defined spatial orientation and depth of penetration into the tissue. In formation of the catheter implantation within the target tissue, catheters can be spaced closely enough together that the distance between them is no greater than about twice the distance over which the bioactive agent can penetrate the tissue under the pressure in a therapeutically effective amount or concentration. Individual catheters or subsets of the catheters can be implanted at different depths, and in different spatial arrangements within the tissue. The catheter system, under the control of the digital navigation and stereotactic system, can direct the vector and/or depth of each individual catheter, or one or more subsets of catheters, as needed to form a spatially defined catheter implantation during the process of catheter insertion.

The bioactive agent, a solution or suspension of which can be introduced into the target tissue via the implanted catheters, can be a radiochemical, a chemotherapeutic agent or other small molecule, an antibody, a protein or peptide, an oligonucleotide aptamer, an antisense oligonucleotide or a small interfering RNA (siRNA). An example of a radiochemical is a small molecule agent radiolabeled with an Auger electron emitter, such as $^{123}$I or $^{125}$I. Examples are $^{123}$I- or $^{125}$I-iodouridinedeoxyriboside ($^{123}$IUDR or $^{125}$IUDR), wherein the radionuclide is incorporated into a chemical entity that is adapted for uptake into the target cells, in which case the short-range Auger electrons exert their destructive effects directly on the DNA within the cell in which they are contained, and with minimal collateral damage to surrounding cells. Another such radiochemical comprises an Auger electron emitter, such as a prodrug of $^{123}$IUDR or $^{125}$IUDR, or another deoxyribonucleoside analogue that releases Auger electrons, such as a nucleoside, or an analog or a prodrug thereof, containing an Auger electron emitting isotope of bromine or astatine.

The catheter system can be used to deploy within the patient's tissues, for example, within a void left by removal of a brain tumor, catheters emplaced into the tissue surrounding the tumor excision site. Alternatively, the catheter system can be used to deploy a catheter or catheters into other tissues being infiltrated or invaded by individual cancer cells or groups of cancer cells, e.g. tissues in and around the esophagus, intestines, bladder, pancreas, head and neck region, the colon, or the rectum. The catheter system can be deployed beneath the capsule of a cancerous prostate gland, or into the tissues surrounding a cancerous prostate gland. Alternatively, the catheter system can be deployed to introduce the bioactive agent into tumor plaques, such as occur in ovarian cancers.

The entire system can be emplaced entirely within the patient's body, such that the liquid supply system and manifold, as well as the catheter guide device and the catheter or catheters are disposed under the patient's skin. Alternatively, the liquid pressurizer and/or liquid reservoir system may be disposed external to the patient's body.

To the extent that the catheter guide device and the catheters come in contact with body tissue, it is preferred that at least the surface of the guide device and catheters be biocompatible, as can be accomplished through the use of appropriate materials of construction. Likewise, to the extent that the liquid supply system is adapted to be disposed within the patient's body, it's exterior surfaces can be biocompatible.

An embodiment of the present invention concerns surgically implanted drug delivery devices comprised of a plurality of catheters, a catheter guide device, and a computerized, digital, electronic, ultrasound or video-assisted tissue navigation system adapted to navigate or position the system prior to or during implantation of one or more catheters into solid tissue, for example, tissues of the brain, head and neck region, esophagus, thorax, intestines, peritoneal cavity, pancreas, retro-peritoneum, pelvis and prostate gland.

The tissue navigation system can include tissue maps, obtained pre-treatment from the patient undergoing treatment, maps obtained from the patient during the course of treatment as the dimensions of the cancerous tissues change, or general anatomical maps as are well known in the art. The tissue navigation system can stereotactically control emplacement of the catheters into the tissue. The navigation can also receive information from a probe, placed in spatial proximity to a catheter guide passageway or tube that informs the system concerning points of insertion and angles desired for emplacement of each catheter to form the catheter implantation in an optimal configuration. The probe can supply the navigation system with video images, such as by means of a fiberoptic lens mounted at the tip of the probe, and a fiberoptic transmission system relaying the image from the lens through the probe to a video sensor of the navigation system. Or, the probe can include a digital camera and electronic transmission means to the navigation system.

An embodiment of the present invention provides a fiber-optic lens or camera, which can be disposed on a probe spatially associated with the catheter or catheter guide system, that serves to enable the surgeon to visually position a catheter or catheter guide system prior to and/or during the emplacement of a catheter or catheters into tissues otherwise hidden from view. Alternatively the lens can be disposed at the end of the probe and connected by a fiberoptic bundle to a camera contained within the external navigation system. The catheter or catheters can then be emplaced in the tissues after the position of the catheter or catheter guide system has been visualized under video-assisted navigation and guidance. The attached fiber-optic camera may be used to determine the optimal position of the inserted catheters with respect to anatomic structures, such as blood vessels and nerve tracks as needed to avoid trauma during implantation.

A catheter or catheter guide device can be adapted to have affixed thereto, for example by a clip or tube adapted for attachment and removal of the fiber-optic camera after the process of insertion of the catheter or catheters into the tissue. Then, the fiber-optic camera can be detached from the catheter, and, optionally, used to emplace other catheters. Alternatively, the fiber-optic camera can be used to guide the emplacement of a preassembled catheter matrix or array into the tissue.

The catheters and/or the catheter guide devices may be used in combination with digital image-based electronic navigation software for use in conjunction with image-based pretreatment planning. The navigation system can be used with accessories to provide for digitalized drug delivery to treatment fields having a wide variety of 3-dimensional shapes. In this context, digitized drug delivery means that the catheter or catheters are arranged to supply a 3-dimensional treatment field that is congruous with a 3-dimensional treatment field that has been mapped using digital images obtained using computerized axial tomography (CT scans), magnetic resonance imaging (MRI), Positron Emission Tomography (PET scans), PET-CT, or other tissue imaging technologies. The 3-dimensional topography of the treatment field (target tissue) is defined prior to treatment, and may be revised during the treatment period to match the changing distribution of disease within the target tissue. Insertion of the catheters can be monitored by these same means.

Radiofrequency (RF) emitting probes are currently used to determine stereotactic coordinates for emplacement of objects within the brain, and such RF emitting probes can be used in conjunction with, for example, a preoperative MRI scan to guide the exact emplacement of an object within a particular region of the brain. An embodiment of the present invention concerns the attachment of an RF emitting probe to a catheter or to a catheter guide device, enabling the optimal positioning of a catheter or catheter guide device prior to emplacing a catheter or catheters into the tissue. The catheter or catheters may be emplaced in the tissues after the position of the catheter or catheter guide device has been optimized under stereotactic guidance of the RF emitting probe attached to the catheter or the catheter guide device. Thus, the attached RF emitting probe may be used to control the depth of insertion of a catheter or catheters, and to determine the optimal position of the inserted catheters with respect to anatomic structures, such as blood vessels and nerve tracks as needed to avoid trauma during implantation.

In an embodiment of the present invention, an RF emitting probe of this type can be used to guide the emplacement of an individual catheter, one or more catheter implantations, or the catheter guide device itself during the operation. For these purposes, the RF emitting probe may be reversibly physically associated with a catheter, catheter implantation, or catheter guide device. The initial positioning and/or final emplacement of the catheters may be guided using the stereotactic coordinates provided by the RF emitting probe and digital navigation software.

A catheter or catheter guide device can be adapted to have affixed thereto, for example by a clip adapted for attachment and removal of the RF emitting probe, which can be activated during the process of insertion of the catheter into the tissue. The point of RF emission is detected, and provides the stereotactic coordinates needed for precise emplacement of the catheter or catheters. Then, the RF emitting probe can be detached from the catheter or catheter guide device, and, optionally, used to emplace other catheters. Alternatively, the RF probe can be used to guide the emplacement of a preassembled catheter matrix or array into the tissue.

In an embodiment of the present invention, an echogenic probe, which can be visualized by ultrasound, may be used to navigate the catheter guide device, or to emplace an individual catheter, multiple catheters, or a catheter array, during the operation. In addition, radiopaque or paramagnetic substances can be included in at least some of the catheters, such as at the tips, to enable visualization of their positioning during and/or after the surgical procedure. Colored dyes, fluorescent dyes, radiopaque substances, or paramagnetic substances can likewise be introduced through the catheters into the tissue to enable visualization of fluid biodistribution during or after the operation.

With or without the use of an RF emitting probe, echogenic probe, fiber-optic camera, or other digital electronic navigation system, a plurality of catheters can be guided to form a spatially defined arrangement within the tissue using a catheter guide device or by using a pre-formed array of catheters. The catheter system can be used to deliver bioactive therapeutic agents directly into tumors or tissues such as those that have been infiltrated by locally invasive, proliferating tumor cells. The bioactive agents include, but are not limited to radioactive compounds, cytotoxic and other small molecule drugs, antibodies, proteins, peptides, oligonucleotide aptamers, antisense oligonucleotides and siRNA.

The inventive catheter system may be used to treat different types of locally advanced solid tumors. The treatment field may include the tumor itself and/or the tissues adjacent to the tumor. In certain situations, such as in patients with brain tumors, the treatment field may be located in the tissue adjacent to a post-surgical tumor resection cavity. Such tissue may be at risk for a tumor recurrence involving progressive invasion by proliferating tumor cells and tumor-associated neovasculature. In this situation, the treatment field includes the brain tissue adjacent to the tumor, and the treatment may be administered before and/or after tumor recurrence.

Local delivery of pharmaceuticals and radiochemicals is seldom performed. One reason is because the use of one or a few catheters results in either a very limited delivery zone based primarily upon diffusion or low flow rates, or a more extensive delivery zone based upon convection (bulk flow, higher flow rates), but with less accurate targeting in and around the tumor. The range and shape of the pharmaceutical delivery zone produced by a single catheter may have unacceptable variability due to tissue inhomogeneity within an organ, variable interstitial pressure, variable capillary density, uneven scarring, and/or variation related to the disease state (e.g. tumor fibrosis). In addition, the target area itself may be very large and irregularly shaped.

One method of overcoming the inherent problems of localized drug delivery is to use multiple catheters, each catheter being responsible for delivery to a small zone. A more uniform treatment field is possible since each individual catheter delivers the therapeutic agent to one part of the treatment field, also referred to as the sub-treatment field. Overlapping sub-treatment fields provide a complete and more uniform treatment field. Multiple catheters can then deliver overlapping zones of the pharmaceutical agent to provide uniform and effective targeting in tissues of different shapes, sizes and densities. Manual placement of numerous individual catheters, without the benefit of a guide device, is a tedious process with inherent difficulties in the exact relative placement of catheters.

The inventive devices can be used to achieve orderly or evenly spaced catheter placement in a treatment field, within a shorter time frame than can be achieved with manually emplaced catheters, and with a much higher degree of spatial accuracy, as is advantageous during surgery when the patient's body tissues, such as the brain, are exposed. Optimal positioning of catheters is important not only to ensure that the infusate gains access to the entire intended treatment field, but also to minimize exposure to uninvolved regions of the tissue or organ.

A plurality of catheters is adapted to remain within the tissue for a period of time. By this is meant that a catheter does not function merely analogously to a syringe needle, which is inserted into tissue, a material injected, and the needle immediately withdrawn. Rather, the catheter or catheter array within the target tissue is left in place for a period of hours, or of days, weeks, or even months, during which a solution of a bioactive agent, such as a radiological agent, is introduced into the tissue under a certain amount of pressure, that is sufficient to enhance permeation of the tissue by the solution. Typically, resistance to liquid flow into tissue is relatively high, so absolute delivery rates are relatively low compared to a typical injection with a hypodermic syringe needle. On the other hand, the rate of liquid flow into the tissue needs to be sufficiently high to generate bulk flow, and thus such flow rates are higher than typically provided by certain types of osmotic pumps or electronic pumps, e.g. pumps used to infuse insulin. In cerebral tissues, bulk flow can be generated at flow rates in excess of 0.5 microliters per minute.

The catheters may be adapted to avoid backflow of infusate from the catheter track and into tissues at the point of catheter entry, and to avoid introduction of infusate into anatomical spaces beyond the treatment field, e.g. cerebral ventricles, leptomeninges, or subdural space in the case of a brain tumor.

The spacing between the catheters forming the array; the relative orientation of the catheters with respect to each other within the array; and the orientation of the catheter array relative to the target tissue can be optimized to expose the entire target tissue to the drug containing liquid during the treatment period. The catheter array is adapted to minimize trauma to tissues in and around the treatment field during implantation of the device, during the treatment period, and during removal of the device.

Catheter arrays are created using catheter systems to direct the implantation of catheter tips into the tissue in the spatially defined implantation, or by inserting pre-formed arrays of catheters into the tissues. The catheter guide devices determine the vector of each catheter and provides control over the depth of catheter penetration into the treatment field. A variety of catheter guide devices are provided, each suitable for application to one or more target tissue types. In certain circumstances, the catheter guide device may remain in place after implantation of the catheter array. In other instances, the device may be removed after implantation.

The formation of a spatially defined catheter array may be facilitated by using computerized, digital, electronic, ultrasound or video-assisted systems that may be attached directly or indirectly to the catheter guide devices or to the catheters. The computerized, digital, electronic, ultrasound or video-assisted systems are used primarily to navigate the catheter guide devices, or to the catheters into position prior to the implantation maneuver. In certain circumstances, the computerized, digital, electronic, ultrasound or video-assisted system component may be removed after implantation, while in other instances it may remain in place after implantation of the catheter or catheters.

The system herein is adapted to provide accurate insertion of arrays of catheters. The dimensions (length, internal and external diameters) of each catheter are determined functionally by several factors including the depth and diameter of the treatment sub-field; the density of catheters within the array; the intent to minimize damage to tissues; and optimal mechanical strength; and ease of implantation.

The use of the inventive catheter system provides an opportunity to implant drug delivery catheters at points inside of the brain tumor cavity, thereby focusing the treatment on regions of the brain that are most likely to harbor residual brain tumor cells while avoiding trauma to regions beyond the tumor. Each catheter can be adapted in shape and size to minimize trauma to neural and vascular structures during and after insertion, for example, from within the tumor resection cavity. Use of modular catheter arrays provides an option to deliver therapeutic liquids into the treatment field using sustained bulk flow as well as a variety of pulsatile or otherwise episodic schedules of administration, including repetitive injections.

Catheter implantation into the target tissue and formation of the catheter implantation within the tissue is achieved by use of a catheter guide device, which can have a biocompatible surface. The catheter guide device is adapted to guide the implantation of catheters in a specific configuration or orientation with respect to each other and with respect to the tissue into which they are implanted. At least some of the catheters can be attached to a base prior to implantation, making a pre-formed array that in certain instances may be directed by the guide device into the tissue. Alternatively, the catheters may be implanted under the direction of the guide device without being attached to a common base. Catheter guidance is accomplished by the use of catheter guide passageways or guide tubes in the guide device. The passageways provide a path to guide the position spatial orientation and vector of the catheters during implantation, and are adapted to allow relative movement of the catheters through their respective passageways during implantation. There can be features allowing the catheters to be locked in place after implantation, and in that case also to be unlocked when removal of catheters is desired.

The catheter guide device may be left in place with the catheters following implantation, or can be removed after the catheters have been implanted. After implantation, the bioactive agent as a solution or a suspension in the pressurized liquid is discharged from the catheters into the surrounding tissue over a period of time, the bioactive agent being therapeutic for a malcondition of the patient. The liquid medium is biocompatible, for example, physiological saline. The bioactive agent can be present in solution, or can be dispersed as a suspension. Adjuvant materials, such as surfactants, preservatives, and the like, can be present in the liquid.

The guide device can include a modular tile, that is, a flat or curved structure or relatively narrow thickness compared to length and breadth, containing one of more catheter guide passageways or tubes, through which catheters can be inserted in directions defined by the passageway or tube, and optionally containing one or more probe openings adapted to accommodate the positioning of a probe tip in close physical proximity to the guide passageway or tube. A plurality of individual modular tiles can be disposed on a flexible mesh, which can be placed on the surface of, for example, an organ into which the catheters are to be emplaced, in order to define a plurality of spatially defined insertion sites for the catheters.

The catheters are implanted within tissue in the vicinity of a tumor, such as an organ containing an advanced stage solid tumor. An example is the brain of a patient with a brain tumor. The catheter releases the bioactive agent such that the agent is concentrated in, and relatively evenly distributed throughout, the tissue that may contain cancerous cells, adjacent to the tumor or to the cavity remaining after surgical debulking of the tumor.

Certain types of cancer such as ovarian can present as tumor plaques on the peritoneum. Surgical resection is not always possible due to the numbers or locations or the plaques. Since these plaques may be "thin", an application of chemotherapeutic agent to a surface has the potential to penetrate the tumor tissue and destroy it. Thus, an embodiment of the invention is adapted to treat the surface of these tumors which in turn treats the whole of the tumor through diffusion of the pharmaceutical into the tumor. The catheter implantations are designed to place a large number of catheters in the area of the tumor to form an array. The size of the array can be quite large and even encompass the majority of the peritoneal cavity. This particular array can be viewed as a dense series of catheters or a mat of catheters that has some protrusions that effectively "irritate or open" the surface and allow better penetration of the pharmaceutical into the tumor plaques.

The implantation of catheter arrays may be performed using a catheter guide device with its guide passageways or tubes positioned inside of the brain tumor cavity. Accordingly, the invention provides methods for creating catheter arrays arranged in a variety of configurations and orientations relative to the surrounding brain tissue. In addition, the arrays have modular assembly features to allow delivery of therapeutic compounds to treatment fields with diverse 3-D shapes and sizes. Once the catheters array is implanted, therapeutic liquids may be introduced directly into the diseased tissues via a manifold that is connected to the plurality of catheters. Some of the devices described herein are assemblies and adapted to permit changing the position of one or more catheters in the array during the course of the treatment.

With fluid fluxes produced from each catheter, the use of the inventive catheter system provides for more controlled and predictable drug delivery into solid tissues (e.g. brain), with minimal backflow, and with a reduced risk of delivering drugs into anatomic regions beyond the intended treatment field. The use of catheter arrays, each supplying a treatment sub-field, provides a method to more predictably and reliably distribute drugs into tissues with less risk of underexposing the "watershed zones" between adjacent treatment sub-fields. This reduces the guesswork that is invariably associated with the surgical placement of a small number of relatively large catheters into tissue surrounding the brain tumor resection cavity. Finally, the use of guide devices to create catheter arrays is adapted for use in many types of solid tumors in addition to brain tumors, as well as in other therapeutic situations where it is medically indicated to suffuse a bioactive agent into a defined volume of tissue at a relatively uniform concentration throughout. For example, as mentioned above, malconditions involving tumor plaques, such as ovarian cancers wherein plaques forming on the peritoneum, can be treated using inventive catheter arrays adapted to cover relatively large, relatively flat tissue surfaces, wherein the plurality of catheters can be adapted to penetrate the plaque to relatively shallow depths compared to, for instance, the depths to which catheters could be implanted in treating tissue surrounding an excised brain tumor.

The present invention will be described with reference to the attached drawings, which are given by way of non-limiting examples. The "target tissue" refers to the diseased tissue into which the catheters are implanted. The "treatment field" is the 3-dimensional domain of tissue to be treated with the entire catheter implantation. The treatment sub-field is the 3-dimensional domain of tissue supplied by a single catheter in the catheter array. The treatment field and target tissue can be the same.

The "solution or suspension of the bioactive agent" is any flowable composition containing a substance (a therapeutic substance) deemed to be useful in the treatment of a disease. The solution may contain one or more therapeutic substances, including but not limited to radioactive compounds, small molecule drugs, antibodies, proteins, peptides, oligonucleotides. The therapeutic substance may be dissolved (solution) or suspended (emulsions, miscelles, liposomes, particles, etc) in the therapeutic liquid. As the term is used herein, a "solution" of a bioactive substance also includes a suspension or a dispersion that is suitable for infusion by way of the catheters. Once the solution enters the tissue, it is referred to as the "infusate."

"Catheters" are hollow or tubular structures, which are implanted directly into the treatment field. A solution of a bioactive agent is introduced into the target tissue (treatment field) via the catheters. Catheters are hollow, having a lumen or central passageway through which the solution flows from the liquid supply system into the tissue. A catheter comprises a tip, and one or more openings, apertures or ports at or relatively near the tip, or on any portion of the catheter adapted to be in direct contact with the tissue. A catheter may be linear or curvilinear, or can be helical, and is adapted for implantation into solid tissue of a patient. The catheter may comprise one or multiple thick segments, rings or bulges on the outside of the shaft to reduce backflow around the catheter track and thus promote uptake of the infusate into the tissue. The catheter may further comprise a non-cutting rounded tip to minimize trauma to tissues during implantation.

The base of the catheter is connected via a manifold to the source of the pressurized liquid containing a pharmaceutical or radiochemical agent. The base of the catheter provides the route for delivery of liquid to the distal end of the catheter, which resides within the tissue after implantation.

Each catheter has a tip that pierces the target tissue. The catheter tip may have an aperture or port (open end) or it may be plugged (closed end). The tip and nearby sections of the catheter can also include ports adapted for emission of the solution. The therapeutic liquid flows through the lumen out of the aperture or port and/or port(s) into the treatment field. A catheter may contain one or more apertures or ports. Ports may be located a various places on the catheter, including the tip and/or the sides.

The catheter tips may be equipped with catheter tip bumpers intended to minimize tissue trauma as the catheter tip pierces the target tissue during insertion. Catheter tip bumpers may be comprised of a hard substance such as metal or a soft polymeric material. Bumpers can have a blunt contour to provide non-cutting dissection of the target tissues. These features reduce the risk of damage to blood vessels and nerve tracts in the path of the catheter tip. Catheters may include expanded sections, bulges, intended to minimize backflow of treatment fluid flowing from the apertures or ports.

The "catheter track" is a passageway formed in the tissue as the catheter is advanced. The catheter track surrounds the catheter following implantation.

A catheter "base" is connected to the source of the solution by means of a manifold. The catheter tip enters directly into the treatment field, and maintains contact with the target tissue, whereas the catheter base does not enter the target tissue. The catheter base may come into contact with tissues outside of the treatment field.

"Flexible joints" may be included in the catheter tubing to reduce potential traction on the target tissues at the point of catheter entry. Flexible joints may be included anywhere in the catheter tubing system or catheter. "Expansion joints" allow compression or expansion of the catheter along its primary linear axis.

"Catheter arrays" are comprised of two or more catheters arranged in a specific configuration. Catheter arrays may have a pre-formed or fixed configuration that is established prior to implantation into the tissue. Alternatively, catheter arrays may be formed during the process of implantation when using a catheter guide device. Catheter arrays can be parallel or radial (positive or negative) arrangements of catheters, or may have a variety of different patterns designed to treat the region around a tumor resection that is prone to tumor recurrence. Some of the alternate designs are described below.

The catheter guide device with its guide passageways or guide tubes accurately guides each catheter into its defined position within the tissue during implantation. A variety of catheter guide devices are described below. Catheter guide devices (a) provide pre-determined spacing between the catheters within a catheter array; (b) determine the relative orientation of the catheters with respect to each other as they enter the treatment field; and (c) determine the relative orientation (i.e. vector) of the catheters with respect to the target tissue.

The catheter guide device can include two or more catheter guide passageways or catheter guide tubes into which the catheters are inserted for implantation. Catheter "guide passageways" provide defined paths for the catheters to follow during implantation, and are adapted to allow relative motion of the catheters through the respective passageways during catheter implantation. During implantation, the catheter tips emerge from the distal or efferent end of the catheter guide. The operator controls, such as by use of the tissue navigation system, implantation of the catheters at the proximal or afferent end of the catheter guide template. A large numbers of catheters can be implanted, for example about 5, or about 10, or about 20, or about 30 individual catheters.

Catheter guide passageways can be linear, curvilinear or dog-legged (i.e. bent) passages, tubes or holes that serve the purpose of directing individual catheters to a site of egress from the catheter guide device. In addition, these passages, passageways give the catheter a vector upon egress from the catheter guide device.

The system may have as few as 2 and as many as several hundred individual catheters (typically between 5 and about 50). The base ends of the catheters are attached to a manifold that is connected to a portal tubing system into which the therapeutic liquid is introduced under pressure. The template passageways may be arranged in a defined pattern located on the afferent aspect of the template, the "catheter hub." The operator can control implantation of the catheters by manipulating the catheter tubes at the catheter hub. After implantation, the afferent or upstream ends of the catheters can be connected to a catheter manifold.

Base or afferent portions of the catheters can converge upon a common chamber referred to as the manifold. The device can provide a mechanism to connect the afferent sections of the catheters to the manifold. The manifold can then be connected to the portal tube, into which the therapeutic liquid may be introduced. The portal tube may terminate outside of the body or beneath the surface of the body. The therapeutic liquid is introduced into the portal tubing system using a mechanical pump, osmotic pump, syringe, or any device capable of generating hydrostatic pressure. Preferably, the manifold is inside the body, but it may also be outside the body.

Modular catheter guide devices, such as those including tiles and mesh, may be arranged in rows, matrices, grids, circles or other patterns to facilitate successive implantation of catheters. The modular guide tiles may be disengaged prior to use or may be used en bloc.

The catheter guide device can be equipped with one or more inflatable balloons or other padding components to minimize displacement of the device after implantation. The balloon is adapted to maintain a snug fit, maintain catheter placement, and to reduce potential traction created by the movement of device components on the surrounding tissues. In some devices, a balloon may be used to compress the catheter arrays against the surrounding tissues (or into the tissues by extending the catheters into position). Balloons may be filled with air, fluid or gels.

There are various geometric variations for the relative vectors that the catheters take while penetrating the target tissue. One is an array of catheters that are all parallel to each other, which allows for concurrent insertion of all the catheters. Another is to have the direction of the catheters determined by catheter guide tubes or catheter guide passageways, in which case the catheters can be inserted individually or in small sets with non-parallel orientation. The guide passageways allow a great variety of directions for individual catheters.

The devices described in this invention are adapted to not only be used in solid tumor resection cavities, but also to be adapted to a wide range of locally advanced solid tumors. In various embodiments, to provide a broader range of catheter placement devices, use is made of shape memory alloys or memory metals such as copper-zinc-aluminum-nickel, copper-aluminum-nickel, or nickel titanium (nitinol) as part of the guidance device gives the flexibility that is needed. The particular desired arrangement of catheter placement can be made by shaping the guide tubes to terminate in that particular arrangement, as discussed below in conjunction with the Figures.

FIG. 1 is a representation of a catheter guide device design using memory metals or memory polymers. Memory metals and polymers are materials with a high degree of hysteresis such that they will spontaneously regain a previously imposed configuration upon heating or release of loading. The memory materials in the guide tubes can conform to the straight interior of the guide passageway, but upon extension from the end, the release of confining pressure and the warmth of the living tissue can serve to allow the material to assume a bend, for example, that was originally imposed on the material. In this design the catheters that enter the tissue (3) are located within memory metal or memory polymer tubes (2) that are in turn extended from a central sleeve (1). An important feature of this device is its ability to retract into a compact configuration for initial entry into a body cavity with minimal damage to healthy tissue.

Figure 2:
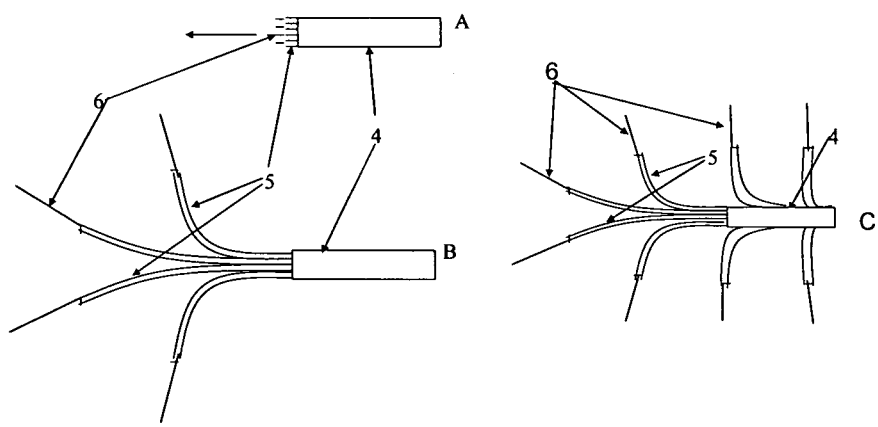
Figure 3:
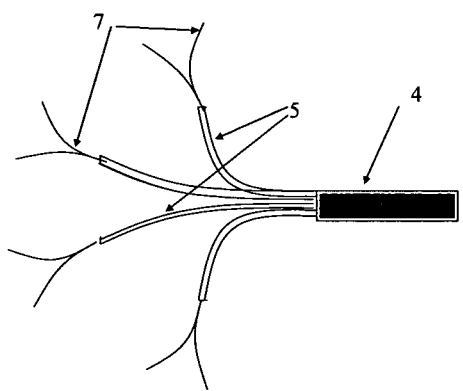
FIG. 3 is a side view of a catheter guide device comprising a guide sleeve (4), extended memory material guide tubes (5), and two catheters (7) per guide tube.
Figure 4:
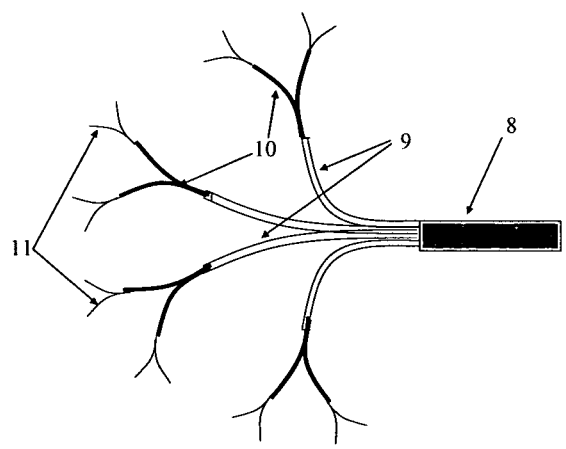
FIG. 4 is a side view of a catheter guide device that includes a guide sleeve (8), a plurality of branching guide tubes (9) and (10), each of which contains a pair of catheters (11).

This embodiment is further illustrated in FIG. 2(A), where the guide tubes (5) are retracted into the sleeve (4) of the device is shown prior to extension into tissue FIG. 2(B) show the now-curved memory material catheter guide tubes extended as into tissue or into a position adjacent to the tissue for insertion of the catheter into the tissue to guide catheter (6) emplacement. FIG. 2(C) shows a similar system of guide passageway with eight guide tubes (5), some of which are disposed laterally to the guide passageway (4) and direct the catheters (6) into tissue in that location. In FIG. 3, a set of catheter guide tubes (7) are shown, each guide tube containing a pair of catheters. In FIG. 4 another level of branching or bifurcation of each catheter guide tube is shown, wherein the sleeve (8) contains two levels of memory metal or memory polymer guide tubes (9 and 10) through which the drug delivery catheters (11) can be extended into the tissue.

Figure 5:
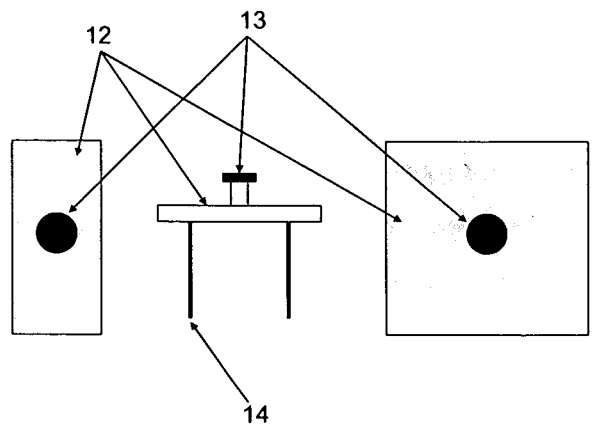
FIG. 5 depicts a guide device adapted to insert catheters straight into a treatment tissue.
Figure 6:
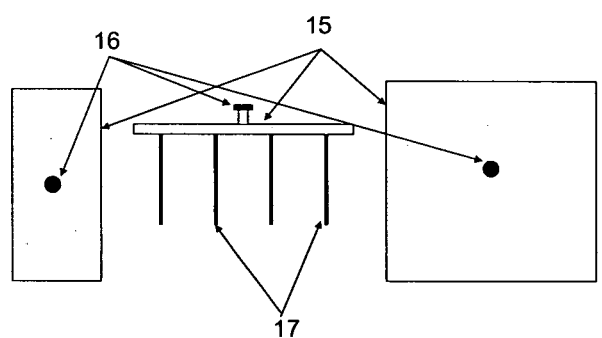
FIG. 6 depicts a guide device adapted to insert catheters straight into a treatment tissue.

In FIG. 5 a set of two or four catheters attached to a guide device, adapted to be inserted at one time, is shown. In FIG. 6 a set of 4 linear catheters or 16 in a square array can be inserted at one time. The catheters (17) are held together by a guide device (15) which also serves as the manifold that connects the liquid supply (16) (which can be through a luer connector) to the catheters.

Figure 7:
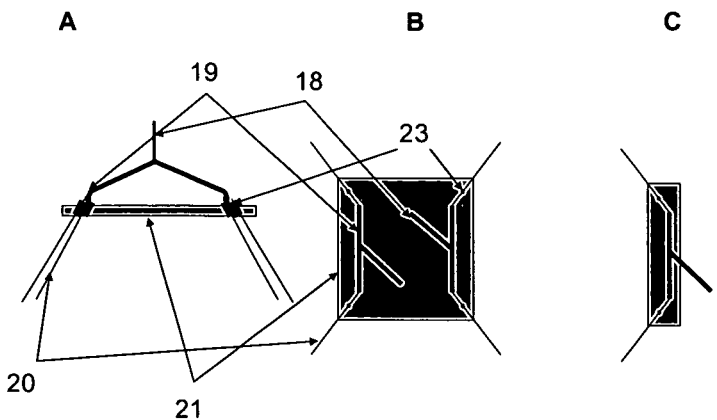
Figure 8:
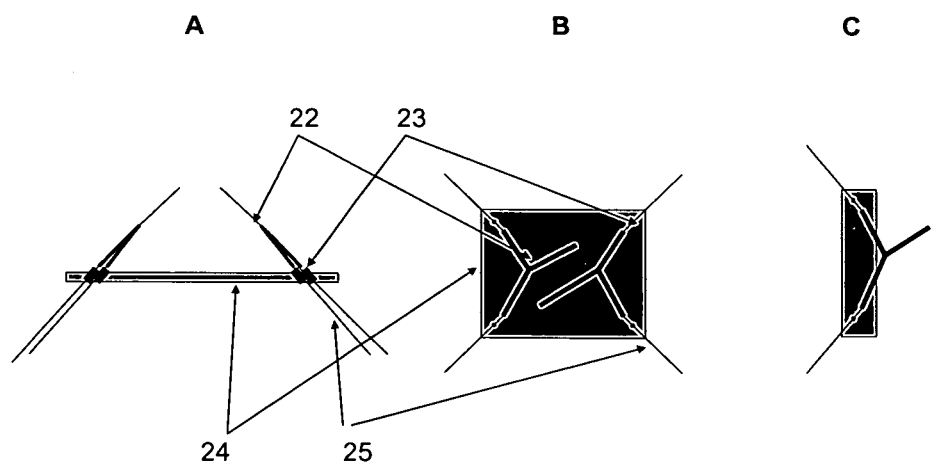

In FIG. 7 a catheter placement device is shown that can be used to insert two or four catheters. The device which can be curved in shape to conform to a body cavity or tumor resection cavity can come in any shape necessary. From the left diagram A is a side view of the device, diagram B is a top view of the device and diagram C is an example of a two catheter placement device. In FIG. 7 the afferent supply side of the device (18) is connected to the efferent tissue distribution catheter (20) via a manifold (19). The support device (21) contains short tubes (23) to guide the final placement of the catheters (20). After insertion of the catheters into position, a holding device can be used at the level of the tubes (23) or manifold (19) to hold the catheters in the tissue and to anchor the device and catheters in place. FIG. 8 is similar to FIG. 7 with the manifold (22) as a Y shaped junction to connect the tissue penetrating catheters to the manifold.

Figure 9:
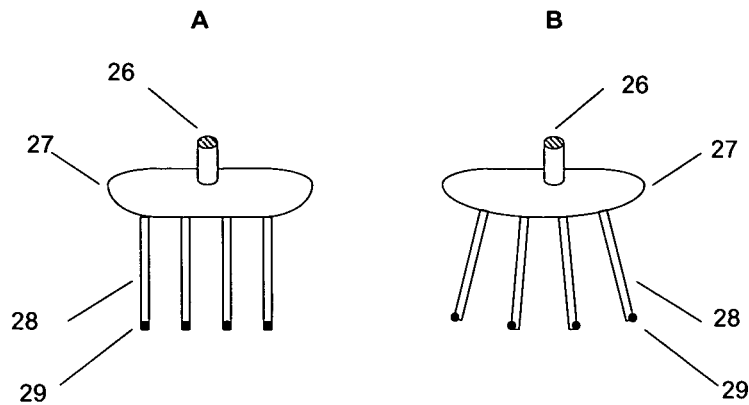

FIG. 9 is an example of a catheter system that uses a implantation device that is expanded during insertion into tissue. This system uses a catheter guide device (27) slowly expands the angles of the catheter tips (29) as the catheters (28) are inserted into tissue. The end result is that the catheters are inserted in radial pattern (diagram B) which facilitates anchoring of the catheters and the device in a single manipulation.

Figure 10:
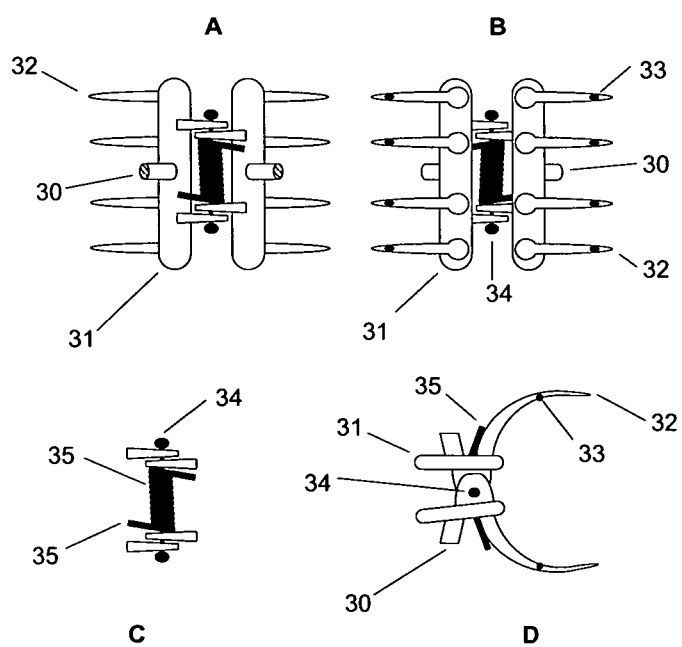

FIG. 10 is an alternate design to implant a series of catheters into a target tissue with a single manipulation. Depending on the size and shape of the target tissue to be treated, a device such as this can be used to treat a segment of tissue with a single manipulation. In this diagram solution supply enters through (30) a port to the manifold (31), into the catheters (32) and finally through the catheter ports (33). The device uses a spring (35) to insert the catheters and the device is held together by a pin (34) connecting the pieces of the device.

Figure 11:
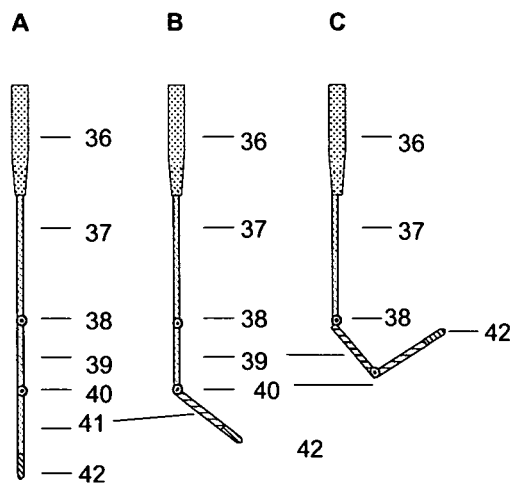

FIG. 11 is an example of a flexible probe. The joints on this device are designed to allow bending to allow access to difficult to reach areas for treatment. The handle (36) is connected to a straight portion followed by an adjustable joint (38) another connecting section (39) a second joint (40) a final extension (41) and the probe (42). The joints on the probe allow the radiofrequency probe to reach tissue spaces that would be difficult with a straight probe.

Figure 12:
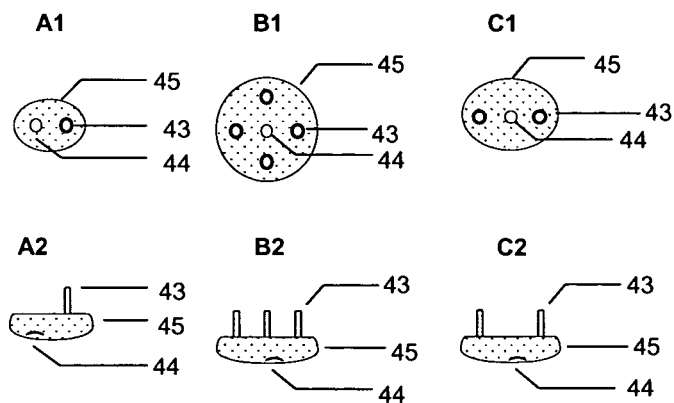
Figure 13:
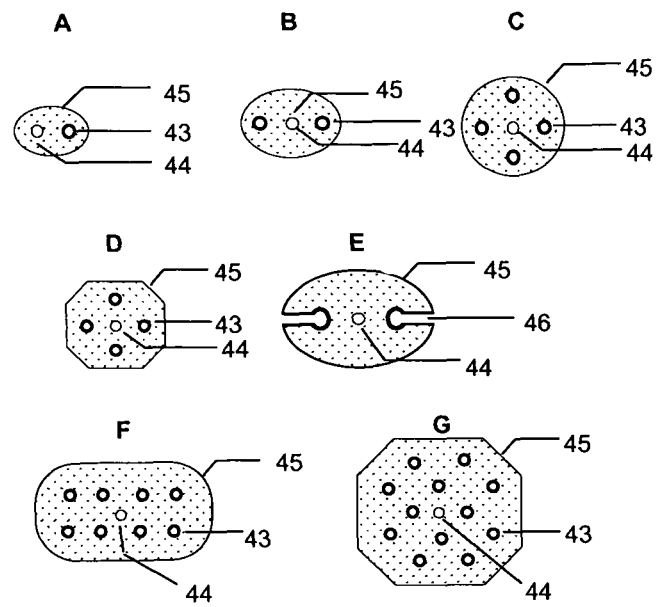

FIG. 12 is a set of guide devices for the insertion of catheters. The device in A is a top view (A1) and a side view (A2) of a guide device designed to be attached to the locating device in FIG. 11. The probe tip in FIG. 11 (42) is designed to be attached to the hole in the catheter guide device of A, B or C (44), the catheter is placed in the guide tubes (43). Different geometries and arrangements are shown in FIG. 13. The body of the device is shown as 45, the guide tubes as 43 and the probe attachment as 44. In FIG. 13 there is also a variation of the guide tube that is open on the side to allow the removal of the catheter from the guide tube (46) such that the body of the device (45) can be removed from the treatment cavity.

Figure 14:
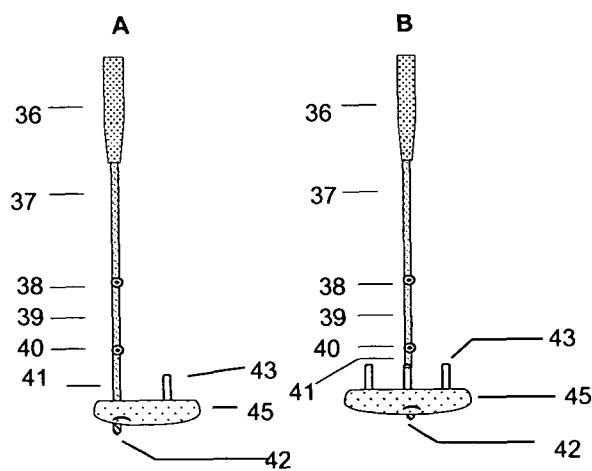
Figure 15:
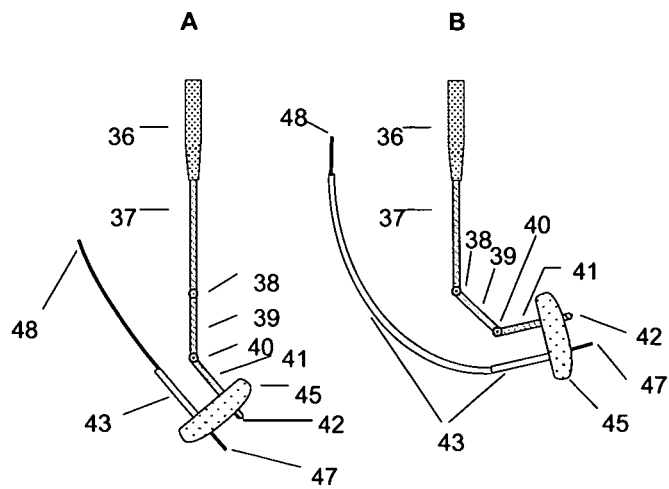

FIG. 14 shows two examples of an assembled device with either one (A) or two (B) catheter guide tubes. As mentioned above the locating probe can be adjusted into a variety of configurations to allow access to different parts of difficult to reach cavities (FIG. 15).

FIG. 16A shows a single catheter being inserted into a body cavity, for example a brain tumor resection cavity, which would be difficult to achieve without a flexible device.

FIG. 16B shows the insertion of a catheter into the posterior lobe of the prostate gland, using a flexible, video-assisted endoscope that has been advanced beyond the recto-vesical fascia between the bladder and rectum. The endoscopic device is equipped with a fiber-optic video system to guide the placement of the catheter template, which is located on the end of the endoscope adjacent to the digital camera. The endoscope may be equipped with a cutting mechanism to facilitate blunt dissection of the tip of the device. Additional features may include an electro-cauterization device, and/or a laser to cut through tissues. Using such a device, catheters may be implanted into various tissues accessible from body cavities using minimally invasive surgical techniques. Most cancers of the prostate gland arise in the posterior lobes (FIG. 16B-1). The anterior aspect of the prostate gland (FIG. 16B-2) is an anatomic landmark used in the pre-treatment planning and in certain instances during the procedure. The seminal vesicles (FIG. 16B-3) are located on the posterior aspect of the prostate gland and are often invaded by cancer cells that have penetrated the posterior capsule of the gland. In the procedure depicted in FIG. 16B, the flexible endoscope device (FIG. 16B-4) is inserted into an abdominal incision (not shown), advanced over the bladder (FIG. 16B-5), and then steered caudally behind the bladder. An accessory cutting device located on the end of the endoscope is used to dissect through the recto-vesical fascia behind the bladder, and thence to the posterior lobes of the prostate gland, which lies between the bladder (FIG. 16B-5) and the rectum (FIG. 16B-6). In certain instances, the surgeon may digitally palpate the prostate gland via the anus (FIG. 16B-7) to facilitate endoscopic manipulations in and around the prostate gland. FIG. 16B-8 shows a catheter emerging from the endoscope, and FIG. 16B-9 shows a fiber-optic video lens that is used to navigate the endoscope within inside of the body cavity as needed to position the catheter guide device, located at the end of the endoscope, into the proximity of the posterior lobes of the prostate gland. Thereafter, the catheter(s) is advanced into the prostate gland, preferably just beneath the capsule, as needed to infuse the fluid pharmacological agent into the interstitial tissues of the prostate gland. In patients with locally advanced prostate cancer, the catheter(s) is advanced into the cancerous peri-prostatic tissues, into which the fluid pharmacological agent is infused.

Figure 17:
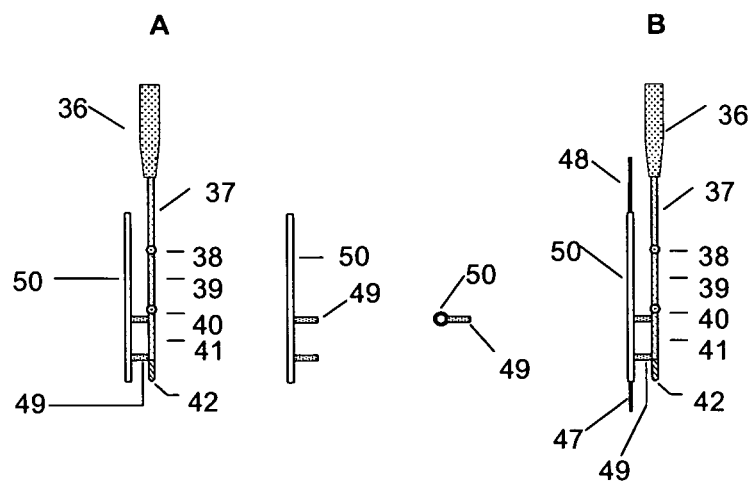

FIG. 17 shows another possible design to use the locating device by attaching a guide tube (50) via connectors (49) that is firmly attached to the distal segment of the locating probe (41). This allows a catheter (47) to be inserted into tissue immediately adjacent to the direction of the locating probe.

Figure 18:
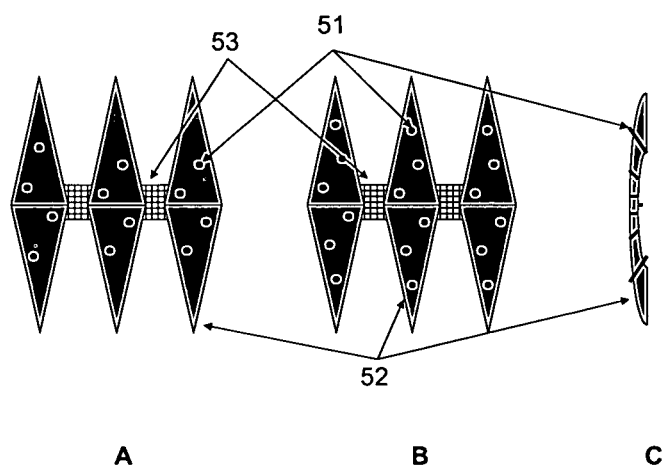
Figure 20:
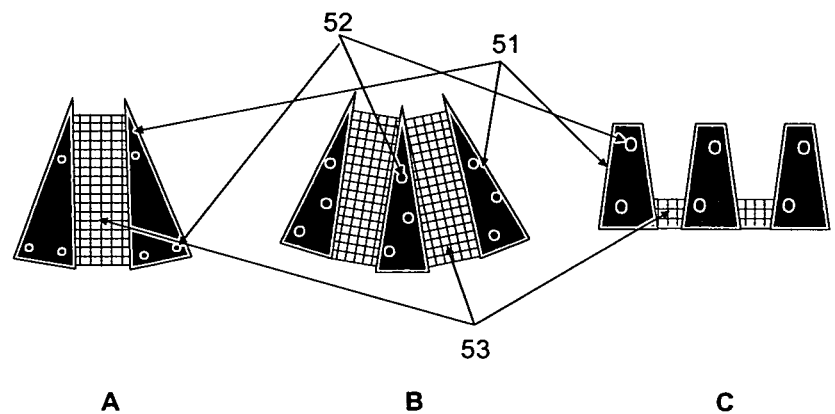

The next series of devices are designed to conform to a hemispherical tumor resection cavity or any oddly shaped region that needs treatment with a series of catheters. For the hemispherical cavities which generally conform to that which is seen in brain tumor resections, a section of a hemispherical shape could conform to the cavity and allow distribution of catheters evenly over the desired treatment area. FIG. 18 is an example of the concept where multiple tiles (52) are held together with a mesh (53) that provides predetermined spacing to aide the surgeon in implanting the catheters through passageways (51) at optimal distances. This spacing ideally includes an area of overlapping between delivery zones. In this example, the catheter guide passageways (51) are encased in a curved or pliable backing tile (52) that allows the catheters to be implanted into the tissue while keeping the catheter guide tubes close to the tissue to be treated. A similar design is shown in FIG. 19 since the tips of the section may not be needed. FIG. 20 shows a device where only the top half of the device in FIG. 18 or 19 are used since we may need only to treat a site of recurrence or there is an oddly shaped resection cavity.

FIG. 21 shows a bottom (A) and a top view (B) of a device that contains two passageways per tile. The biocompatible device has a mechanically firm tile (54) that holds the catheter guide passageways (55) that control the direction of catheter insertion. There is also a mesh (56) connected between the tiles that aides the surgeon in spacing the individual tiles into place and thus providing the desired spacing between catheters for optimal drug delivery zone overlap. In FIG. 22 it is shown that the individual tiles can be cut apart and separated to produce any number of different geometries or as single devices to cover the desired treatment zone.

As described for FIG. 18 it is desirable to have the tiles pliable or conformable to the area of treatment. In FIG. 23 we see that this device is malleable to form rounded surfaces to conform to a resection cavity. In FIG. 23 we see the same device being curved from B to C to D. This device can then be inserted into a resection cavity (59) such as in FIG. 24, conforming to the surface of the cavity (56 and 59) and the drug delivery catheters extended (58) into the tissue. In this figure the different vectors of insertion of the catheters are such that there is an anchoring effect since the catheters can not be easily removed. Treatment can then flow from through the catheters (57) and into the tissue to be treated (58). FIGS. 25, 26 and 27 show a variety of different geometries for the tiles attached to the underlying mesh.

The catheter guide tubes or guide passageways in the designs for FIGS. 7, 8, and 18 through 27 can be of various lengths and provide direction for the final placement of the catheters. These guide passageways can be perpendicular to the guide plate or at any angle with respect to the guide plate or device. Similarly the "mesh" can be made with bars, fine mesh, individual strands, or any other mechanism that retains the relative orientation of the individual guide plates.

Treatment of different tumor cavities and tumor types will necessitate the use of a variety of different catheter lengths which will need to be bundled into a common manifold to allow treatment fluid to reach the ends of the catheters and into tissue. Although this can be accomplished in a variety of ways depending on how many catheters are used for the particular treatment, the manifold can be located anywhere from close to the catheter tips to immediately next to the pump. The manifold can be a T connector or can be a more complicated system that incorporates the inclusion and exclusion of catheters depending on if they are to be used. In an embodiment, different levels of flow constriction are incorporated into the manifold design. Thus, flow rates can be controlled on individual catheters depending on where the catheters were placed. One design for the manifold is shown in FIGS. 28 and 29, the catheters that lead to tissue (60) are fixed in the device after the length is determined and held in place by a sealing device (61) that holds the catheter and seals it in the device. The catheter can then be crimped closed (63) to separate it from the unneeded portion of the catheter that is clipped off and discarded (64 and 65). A hole is then punctured into the catheter (62) by a device that opens the catheter to the fluid source. The drug can then flow from the reservoir into the catheter by backing off the puncturing device and allowing the opening to be exposed to the fluid source (66). Alternatively, the puncturing device can contain an orifice similar to a hypodermic needle and seals into the catheter material, the drug solution could then flow through the needle and into the catheter to the target tissue (67). Another embodiment is to use a housing that incorporates excess catheter length as a coil or a device that stores the excess catheter material in a separate container as in FIG. 30. In this embodiment, there is a catheter (68) that is extended through an optional guide tube (69) and the excess catheter is wound up within the housing (70) that could be inconspicuously flat and left subcutaneously.

FIGS. 28 and 29 show an example of a catheter manifold that can also trim excess catheter material and both seal the emplaced section of catheter and connect it to the manifold for liquid flow. In FIGS. 28 and 29, the manifold takes the catheter that is connected to the tissue for treatment (60) and seals it off from the undesired excess catheter material (63), cuts off the excess catheter material (65) which is then discarded. A connection can then be made to the catheter lumen by puncturing the catheter (62) and either flowing treatment through the puncture site (66). Alternatively, if the puncturing device is a needle that seals at the site of puncture where the needle enters through a self sealing septum providing a seal to prevent leakage (67) then the treatment solution can flow through the needle into the catheter. In FIG. 30 an alternate manifold design is described where the excess catheter length is incorporated into a loop or coil to keep the material neat and organized. In this design the catheter material (68) is coiled in a housing (70) that can be placed under the skin.

In FIG. 31, a balloon is provided to fill a resection cavity, conform to the cavity, and finally extend catheters into tissue for treatment. Such a design can to conform to the space, but preferably not exert pressure on the tissue. If the cavity is spherical or has a defined shape, then it is possible to have a fairly rigid membrane that is inflated and serves as a platform to extend the catheters into the tissue. However, since most cavities are of irregular shape the balloon will need to conform to an irregularly shaped cavity. Thus the membrane forming the balloon can be flexible with minimal rigidity and more readily conformable to different cavities. This irregularly shaped membrane can be held in place by a solution, gas or preferably a gel. This gel can be made to solidify in situ by using a thermosetting gel such as a biocompatible water based gel that is a solution at low temperature and forms a solid gel at body temperature. The gel can be adjusted in terms of viscosity by using different compositions and concentrations. An example of a gelling material is a Pluronic® material. It is also possible to have a system that uses an inflatable or expandable primary membrane that has catheters incorporated into its surface, wherein the catheters are extended by a second inflation. FIG. 31 illustrates one possible expandable catheter placement device. This device has an expandable membrane (73) that is shown as spherical in the drawing, but could be inflated to conform to an irregularly shaped cavity. It has integrated guide passageways connected to the surface of the expandable membrane (74) that provide the final guidance and placement of the drug delivery catheters (75). A primary guide tube system (72) is also integrated into the main body of the device (71) to provide initial placement and direction to the drug delivery catheters.

The liquid supply system can be connected to the catheters via a manifold to allow the fluid to be distributed to all of the catheters. The rate of flow to all the catheters can be equal, or some catheters (a first subset) can have a liquid flow rate different from other catheters (a second subset). As described in a previous patent application, this can be achieved by a flow constrictor such that there is sufficient pressure upstream from the constriction compared to the low pressure side connected to the tissue port. This excess pressure on the supply side of the flow constrictor ensures constant flow to all catheters. Another embodiment uses flow restrictors of different sizes to control different flow to different catheters. Differential flow can be valuable when treatment to one zone of tissue needs to be less intense due to location of critically sensitive tissue, such as a brain catheter that is close to the subventricular zone where it is desired to minimize treatment. Alternatively, it may be desired to increase the treatment zone in areas where there is no critically sensitive tissue and in these regions a wider treatment zone achieved with higher flow rates may result in better therapeutic outcomes.

The liquid supply system is adapted to ensure one way flow, since reverse flow (backflow) could cause contamination in the manifold or to other catheters. In various embodiments, the a one way valve such as a duck bill or flapper valve is incorporated either in the manifold or somewhere along the length of the catheter. Equally important is the need to keep the catheters open and prevent clogging of the catheters during reactive tissue encapsulation. The catheters can be kept open by a trickle flow of drug or saline to help prevent the tissue from growing into the catheter openings. The need for a trickle flow can also be used in conjunction with intermittent flow to catheters since a rotating valve could be used to send drug treatment to a subset of catheters while infusing saline to the rest of the catheters. Thus there can be a constant flow of fluid to all catheters. This device can be incorporated into the manifold as a rotating valve. In one embodiment of the invention a valve could be supplied with drug and normal saline as two separate feed streams. The two separate feed streams can be directed to different catheters: drug would be delivered to one set of catheters and saline to keep the catheters open would be sent to the other catheters, after a period of time the saline catheters would then deliver drug and the catheters that were delivering drug would switch to saline to keep the catheters open.

The fluid pharmacological agent can be discharged repetitively or intermittently from the catheters into the tissues as a result of temporary increases in the fluid pressure generated by the infusion pump. The increased fluid pressure can be instantaneous or brief in duration, for example in a stepwise or gradual waveform such as a square wave or sinusoidal, thereby producing a rapid injection of the fluid pharmacological agent into the tissue. Alternatively, the pressure gradient can be more sustained, but not maintained continuously throughout the delivery of the agent, thereby producing one or more fluid waves that carry the fluid pharmacological agent into the tissue. In either case, the intervals between the repetitive or intermittent discharges of fluid can be brief (e.g. one second) or longer (e.g. several days).

Alternatively, the fluid pharmacological agent can be discharged continuously from the catheters into the tissues as a result of a continuous pressure gradient generated and maintained by the infusion pump. The pressure gradient can be maintained throughout the delivery of the agent, thereby producing continuous bulk flow of the fluid pharmaceutical agent into the tissue. The fluid pressure can be increased in one or more steps, increased continuously over at least part of the infusion period, or increased over all of the entire infusion period.

As another alternative, the pharmaceutical solution can be injected as rapid pulses that may disrupt intercellular interactions sufficiently to allow an increased level of bulk flow around the catheters. These pulses can be subsonic to approaching ultrasonic levels.

According to another embodiment of the invention, the fluid pharmacological agent may be discharged as a brief injection, a pulse, or as a more sustained infusion into the tissues, and then followed by an infusion of fluid that does not contain the fluid pharmacological agent. The fluid lacking a pharmacological agent may be introduced into the tissue by one or more instantaneous injections, one or more sustained waves of fluid movements, or by continuous bulk flow that is maintained by a constant pressure gradient.

The present invention also discloses bioactive agents that can be delivered using the inventive system or method. The bioactive agent can be a radiochemical, chemotherapeutic agent or other small molecule, antibody, protein, peptide, oligonucleotide aptamer, antisense oligonucleotide or a small interfering RNA (siRNA).

An example of a radiochemical that can be delivered using the devices described herein is an Auger electron emitter, such as $^{123}$I- or $^{125}$I-iodouridinedeoxyriboside ($^{123}$IUDR or $^{125}$IUDR). In this example, a radioactive $^{123}$I- or $^{125}$I-atom has been incorporated into a chemical entity, e.g. uridine deoxyribonucleoside, which is adapted for cellular uptake and incorporation into newly synthesized DNA in the target cells. In this example, target cells are defined as any cell in the treatment field engaged in DNA synthesis. Once incorporated into the chromosomes, the short-range Auger electrons are optimally located to exert their destructive effects directly on the DNA in the cell in which they are contained, and with minimal collateral damage to surrounding cells.

Numerous Auger electron emitting deoxyribonucleosides may be used, including but not limited to: 5-[$^{125}$I]-iodouridine 2'deoxyribonucleoside, 5-[$^{123}$I]-iodouridine 2'deoxyribonucleoside, 5-[$^{124}$I]-iodouridine 2'deoxyribonucleoside, 5-[$^{77}$Br]-bromouridine 2'deoxyribonucleoside, 5-[$^{80m}$Br]-bromouridine 2'deoxyribonucleoside, 8-[$^{125}$I]-iodoadenine 2'deoxyribonucleoside, 5-[$^{80m}$Br]-bromoadenine 2'deoxyribonucleoside or 5-[$^{211}$At]-astatine uridine 2'deoxyribonucleoside.

A prodrug of the above-mentioned nucleoside analogues can also be delivered using the devices and methods disclosed herein. This includes phosphate and carboxylate esters of the 5' and 3' hydroxyl groups on the ribose moiety of the nucleosides. Such prodrugs can be hydrolyzed in situ, releasing the active forms of such nucleosides, which after uptake by cells, are re-phosphorylated, recognized by cellular DNA polymerases and then incorporated into newly synthesized DNA. It is understood that a variety of chemical modifications of the nucleoside analogues containing the Auger electron emitting nuclides described above may be delivered using the devices disclosed herein. For example, nucleosides containing a 3' deoxyribose may be incorporated at the terminal position of a growing strand of DNA prior to chain termination. Finally, it is understood that the ribose or base moieties of deoxynucleoside analogues such as $^{123}$IUDR or $^{125}$IUDR may be modified in numerous ways without necessarily interfering with their incorporation into newly synthesized DNA.

All publications, patents, and patent documents cited in the specification are incorporated by reference herein, as though individually incorporated by reference. In the case of any inconsistencies, the present disclosure, including any definitions therein, will prevail. The invention has been described with reference to various non-limiting examples and embodiments. However, it should be understood that many variations and modifications may be made while remaining within the spirit and scope of the present invention.

What is claimed is:

1. A catheter system for delivery of a pressurized liquid solution or suspension containing a bioactive agent via a spatially defined catheter implantation into a targeted body tissue comprising a tumor, tumor plaque or tissue adjacent to a surgical tumor resection cavity of a patient; the system comprising:

a plurality of biocompatible catheters, each catheter being hollow, and linear, curvilinear, or helical; each catheter being adapted for insertion into the body tissue and for bulk flow or convection-enhanced delivery of the solution or suspension of the bioactive agent through the catheter into the tissue; and the catheter system comprising a catheter guide device comprising a plurality of modular tiles, wherein each tile comprises a plurality of passageways therethrough, each modular tile being adapted for emplacement on a respective portion of a surface of the target tissue for guiding insertion of each of the biocompatible catheters through the respective passageway into the tissue to form a spatially defined catheter implantation;

wherein as directed by the catheter guide device each catheter is emplaced within the tissue individually, in subsets of a plurality of catheters, or all of a plurality of catheters concurrently, to provide the spatially defined implantation such that the pressurized solution or suspension of the bioactive agent is delivered through each catheter thereby providing the bulk flow or convection-enhanced delivery within a volume of target tissue;

the catheter system further comprising a pressurized liquid supply system adapted for delivery of a pressurized liquid via a manifold to each of the plurality of catheters; wherein the liquid supply system comprises a pressurizer adapted to apply a pressure to a liquid solution and a manifold to deliver the liquid under pressure to each of the plurality of catheters such that the liquid can pass through each catheter into the targeted body tissue.

2. The catheter system of claim 1 comprising a catheter guide device wherein at least some of the plurality of modular tiles are disposed on a flexible mesh.

3. The catheter system of claim 2 wherein the catheter guide device comprising the plurality of tiles disposed on the mesh, is adapted by cutting to size, bending to shape, or arranging in a geometric pattern that conforms to the contours of a surface of a tumor surgical resection cavity, tumor plaque, or other tumor surface to allow distribution of the catheters within the target tissue.

4. The catheter system of claim 2 wherein the tile or the mesh is adapted to be cut or trimmed.

5. The catheter system of claim 1 further comprising an electronic, radiofrequency, ultrasound, or video-assisted computerized digital tissue navigation system adapted for guiding the emplacement of the biocompatible catheters to form the spatially defined implantation within the targeted body tissue.

6. The catheter system of claim 5 wherein the system further comprises pre-treatment organ maps of the patient, maps obtained from the patient during the course of treatment as tumor dimensions change, or general anatomical maps, or any combination thereof, wherein the maps are used by the system in guiding emplacement of the biocompatible catheters.

7. The catheter system of claim 5 wherein the tissue navigation system comprises a probe adapted to be placed adjacent to the targeted body tissue or within the targeted body tissue to inform the tissue navigation system by transmission of electronic, radiofrequency, ultrasound, or video data to the tissue navigation system such that the tissue navigation system provides information directing emplacement of the catheters.

8. The catheter system of claim 7 wherein the probe is bendable.

9. The catheter system of claim 7 wherein the probe is substantially rigid, and is straight or curved.

10. The catheter system of claim 7 wherein a tip of the probe comprises a digital camera or a fiberoptic lens and the probe comprises an electronic link or fiberoptic transmission filaments respectively adapted for connection to the tissue navigation system.

11. The catheter system of claim 7 wherein a tip of the probe comprises an ultrasound transponder.

12. The catheter system of claim 7 wherein the probe is further adapted to provide surgical functions to assist in emplacement of the catheters.

13. The catheter system of claim 12 wherein the probe comprises scissor, straight blade, rotary blade, cutting laser, or electrocautery tools, or a combination thereof.

14. The catheter system of claim 7 wherein the probe is adapted to be steered or directed within a patient's body from the exterior of the body.

15. The catheter system of claim 14 wherein the tissue navigation system is adapted to steer or direct the probe within the patient's body.

16. The catheter system of claim 7 wherein each of the plurality of tiles further comprises a probe opening therethrough adapted to removably hold the probe in close proximity to a point of entry of a catheter into the tissue.

17. The catheter system of claim 1 wherein a plurality of catheters are adapted for concurrent insertion.

18. The catheter system of claim 1 wherein the manifold and the plurality of catheters are connected prior to insertion of the catheters into the tissue.

19. The catheter system of claim 18 wherein the plurality of catheters are inserted into the tissue concurrently, and the manifold is adapted to remain in place adjacent to the tissue during administration of the pressurized liquid to the tissue such that the catheters and the manifold together provide an anchoring effect on the catheters within the tissue.

20. The catheter system of claim 1 comprising a substantially flat planar or conformable guide device adapted to remain in place adjacent to the tissue during administration of the pressurized liquid wherein a first subset of the plurality of catheters is inserted at one angle through a tile of the guide device, and a second subset of the plurality of catheters is inserted at a second angle through a tile of the guide device, wherein the first angle and the second angle with respect to the guide device are not identical, to provide an anchoring effect to the tissue.

21. The catheter system of claim 20 wherein the guide device is flat planar, the first subset of catheters is disposed at an angle of less than 90 degrees with respect to the guide device and the second subset of catheters is disposed at an angle of greater than 90 degrees with respect to the guide device such that the catheters are splayed to provide the anchoring effect.

22. The catheter system of claim 20 wherein the guide device is conformable to the tissue and a first subset of catheters is disposed within the tissue at a first vector and a second subset is disposed within the tissue at a second vector, and the first vector and the second vector are not congruent.

23. The catheter system of claim 1 wherein the manifold comprises a plurality of catheters affixed thereto, where there is a relative angle between adjacent catheters that increases as the catheters are inserted into the tissue.

24. The catheter system of claim 1 wherein the manifold comprises a spring adapted to apply pressure such that the plurality of catheters attached to the manifold penetrates into the tissue.

25. The catheter system of claim 16 wherein at least some of the catheter guide passageways, the probe opening, or both, are adapted to allow removal of the tile from around the catheter, the probe, or both.

26. The catheter system of claim 1 wherein the catheter guide device is adapted to trim excess catheter material and to connect one or more of the catheters to a manifold.

27. The catheter system of claim 1 wherein a tile further comprises a probe opening therethrough adapted to removably hold the probe in close proximity to a point of entry of a catheter into the tissue.

28. The catheter system of claim 1 wherein the bioactive agent comprises an Auger-electron emitting radionucleoside or an analog or a prodrug thereof.

29. The catheter system of claim 28 wherein the radionucleoside or analog or prodrug thereof is a halogenated nucleoside analog.

30. The catheter system of claim 29 wherein the radionucleoside or analog or prodrug thereof comprises 5-[$^{123}$I]-iodouridine 2'-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine 2'-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine 2'-deoxyribonucleoside, 8-[$^{125}$I]-iodoadenine 2'-deoxyribonucleoside, 5-[$^{77}$Br]-bromoadenine 2'-deoxyribonucleoside, 5-[$^{80m}$Br]-bromoadenine 2'-deoxyribonucleoside or 5-[$^{211}$At]-astatouridine 2'-deoxyribonucleoside.

31. The catheter system of claim 1 wherein the bioactive agent comprises an Auger-electron emitting nucleoside prodrug.

32. The catheter system of claim 31 wherein the prodrug comprises a 3'- or 5'-phosphate or carboxylate ester of a deoxyribosyl or ribosyl moiety of the radionucleoside.

33. The catheter system of claim 1 wherein the bioactive agent comprises a second medicament.

34. A method of emplacement of a spatially defined catheter implantation adapted for delivery of a pressurized liquid containing a bio active agent comprising an Auger-electron emitting radionuclide to a volume of body tissue comprising a tumor, tumor plaque or tissue adjacent to a surgical tumor resection cavity, the method comprising,
  disposing a plurality of tiles on a surface of the body tissue comprising the tumor, tumor plaque or tissue adjacent to a surgical tumor resection cavity, then directing the emplacement of a plurality of biocompatible catheters into the body tissue through a plurality of respective tiles such that the spatially defined catheter implantation is provided, then,
  connecting a source of a pressurized liquid containing a solution or suspension of the bioactive agent comprising the Auger-electron emitting radionuclide to the plurality of biocompatible catheters, then
  delivering the pressurized liquid under pressure from the source to the biocompatible catheters, such that the pressurized liquid containing the bioactive agent passes through the biocompatible catheters under pressure into the body tissue to provide bulk flow or convection-enhanced delivery of the Auger electron-emitting bioactive agent to the tissue comprising the tumor, tumor plaque, or tissue adjacent to the surgical tumor resection cavity.

35. The method of claim 34 wherein the tumor, tumor plaque or tissue adjacent to the surgical tumor resection cavity comprises a cancer of brain, head or neck, esophagus, prostate, ovary, liver, pancreas, bladder, colon, or rectum.

36. The method of claim 34 wherein the radionuclide is $^{77}$Br, $^{80m}$Br, $^{123}$I, $^{124}$I, $^{125}$I, or $^{211}$At.

37. The method of claim 34 wherein the bioactive agent comprises an Auger-electron emitting radionucleoside or an analog or a prodrug thereof.

38. The method of claim 37 wherein the Auger-electron emitting radionucleoside or analog or prodrug thereof is a halogenated nucleoside analog.

39. The method of claim 38 wherein the Auger-electron emitting radionucleoside or analog or prodrug thereof comprises 5-[$^{123}$I]-iodouridine 2'-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine 2'-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine 2'-deoxyribonucleoside, 8-[$^{125}$I]-iodoadenine 2'-deoxyribonucleoside, 5-[$^{77}$Br]-bromoadenine 2'-deoxyribonucleoside, 5-[$^{80m}$Br]-bromoadenine 2'-deoxyribonucleoside or 5-[$^{211}$At]-astatouridine 2'-deoxyribonucleoside.

40. The method of claim 34 wherein the bioactive agent comprises an Auger-electron emitting nucleoside prodrug.

41. The method of claim 40 wherein the Auger-electron emitting nucleoside prodrug comprises a 3'- or 5'-phosphate or carboxylate ester of a deoxyribosyl or ribosyl moiety of the Auger-electron emitting radionucleoside.

42. The method of claim 34 wherein the bioactive agent comprises a second medicament.

43. The method of claim 34 further comprising using an electronic, radiofrequency, ultrasound, or video-assisted computerized digital tissue navigation system adapted for guiding the emplacement of the plurality of biocompatible catheters to form the spatially defined catheter implantation within the targeted body tissue.

44. The method of claim 43 wherein the system further comprises pre-treatment organ maps of a patient, maps obtained from the patient during the course of treatment as the tumor dimensions change, or general anatomical maps, wherein the maps are used by the system in guiding emplacement of the biocompatible catheters.

45. The method of claim 43 wherein the system further comprises a probe adapted to be placed adjacent to the targeted body tissue or within the targeted body tissue to inform the system by transmission of electronic, radiofrequency, ultrasound, or video data to the system, wherein the probe transmits location information to the system to control or guide emplacement of the biocompatible catheters.

46. The method of claim 45 wherein a tip of the probe comprises a fiberoptic lens and the probe comprises fiberoptic transmission filaments adapted for connection to the system, wherein a fiberoptic video image is transmitted from the probe to the system to control or guide emplacement of the biocompatible catheters, or comprises a digital camera that electronically transmits image data to the system.

47. The method of claim 45 wherein a tip of the probe comprises an ultrasound transponder, wherein ultrasound image data is transmitted from the probe to the system to control or guide emplacement of the biocompatible catheters.

48. The method of claim 45 wherein the probe is further adapted to provide surgical functions to assist in emplacement of the biocompatible catheters, and wherein prior to, during, or after the emplacement of at least some of the biocompatible catheters within the body tissue, surgical functions are carried out using the probe.

49. The method of claim 48 wherein the probe comprises scissor, straight blade, rotary blade, cutting laser, or electrocautery tools, or a combination thereof.

50. The method of claim 45 wherein the probe is adapted to be steered or directed within a patient's body from the exterior of the patient's body, and wherein prior to or during, or both, the emplacements of at least some of the biocompatible catheters within the body tissue, the probe is steered or directed into a position adjacent to the tissue to inform emplacement of the biocompatible catheters.

51. The method of claim 50 wherein the system steers or directs the probe within the patient's body prior to or during, or both, the emplacement of the biocompatible catheters within the body tissue.

52. The method of claim 45 wherein a tile further comprises using a probe opening therethrough is adapted to removably hold the probe in close proximity to a point of entry of at least one of the biocompatible catheters into the tissue, wherein the probe is emplaced within the probe opening of the modular tile to guide emplacement of a biocompatible catheter, then the biocompatible catheter is emplaced into the tissue through the respective catheter guide of the modular tile.

53. The method of claim 34 further comprising using a catheter guide device comprising the plurality of tiles comprises at least one adaptable tile that can be cut, trimmed or bent to a desired shape or size with desired contours and a desired number of passageways, or comprises a plurality of tiles disposed on a flexible mesh that can be cut, trimmed or bent to a desired contour, shape, or size to fit the target tissue.

54. The method of claim 34 further comprises using a modular tile disposed on and connected to a mesh, the mesh being adapted to hold the plurality of modular tiles in a relative spatial disposition when the mesh and modular tiles are disposed on a surface, wherein prior to emplacement of the biocompatible catheters, the mesh with the modular tiles disposed thereon is disposed on a body surface or an organ surface through which the biocompatible catheters will be emplaced into the tissue.

55. The method of claim 54 wherein at least some of catheter guide passageways, a probe opening, or both, are slotted to allow removal of at least some modular tiles from around the biocompatible catheters, the probe if present, or both, and wherein after emplacement of the biocompatible catheters, at least some of the tiles are removed from the surface.

56. The method of claim 34 further comprising using a catheter guide device is adapted to trim excess catheter material and to connect the plurality of biocompatible catheters to a manifold and wherein, after emplacement of the biocompatible catheters, the excess catheter material is trimmed away and the biocompatible catheters are connected to the manifold using the guide device.

57. The method of claim 34 wherein the pressurized liquid flows through each of the plurality of biocompatible catheters at a substantially equal rate.

58. The method of claim 34 wherein the pressurized liquid flows through a first subset of the plurality of biocompatible catheters at a different rate than the rate at which the liquid flows through a second subset of the plurality of biocompatible catheters.

59. The method of claim 58 wherein the first subset of biocompatible catheters and the second subset of biocompatible catheters are adapted to control the respective flow rates therethrough to provide a relative differential flow rate between the first subset and the second subset.

* * * * *

UNITED STATES PATENT AND TRADEMARK OFFICE
CERTIFICATE OF CORRECTION

PATENT NO. : 8,600,479 B2
APPLICATION NO. : 12/531808
DATED : December 3, 2013
INVENTOR(S) : Dalke et al.

It is certified that error appears in the above-identified patent and that said Letters Patent is hereby corrected as shown below:

On the title page, in column 1, under "(75) Inventors", line 6, delete "L" and insert --L.--, therefor On the title page, in column 2, under "(56) Other Publications", line 1, before "International", insert --"--, therefor On the title page, in column 2, under "(56) Other Publications", line 2, after "2008", insert --"--, therefor On title page 2, in column 1, under "(56) U.S. Patent Documents", line 40, after "Dalke et al.", insert --¶2002/0120238 A1 8/2002 James Jr. et al.
2008/0004630 A1 1/2008 Badie
4,657,536 4/1987 Dorman
5,211,165 5/1993 Dumoulin et al.
5,882,332 3/1999 Wijay
6,217,554 B1 4/2001 Green--, therefor On title page 2, in column 1, under "(56) Foreign Patent Documents", line 9, after "11/2008", insert --¶WO WO-99/02859 A1 1/1997
WO WO-00/67647 A1 11/2000--, therefor On title page 2, in column 1, under "(56) Other Publications", line 1, before "International", insert --"--, therefor On title page 2, in column 1, under "(56) Other Publications", line 2, after "2008", insert --"--, therefor On title page 2, in column 1, under "(56) Other Publications", line 3, before "International", insert --"--, therefor On title page 2, in column 1, under "(56) Other Publications", line 4, after "2008", insert --"--, therefor Signed and Sealed this
Seventeenth Day of June, 2014

Michelle K. Lee
*Deputy Director of the United States Patent and Trademark Office*

On title page 2, in column 1, under "(56) Other Publications", line 6, before "International", insert --"--, therefor On title page 2, in column 1, under "(56) Other Publications", line 7, after "2008", insert --"--, therefor On title page 2, in column 1, under "(56) Other Publications", line 8, before "International", insert --"--, therefor On title page 2, in column 1, under "(56) Other Publications", line 9, after "2008", insert --"--, therefor On title page 2, in column 1, under "(56) Other Publications", line 10, before "International", insert --"--, therefor On title page 2, in column 1, under "(56) Other Publications", line 11, after "2008", insert --"--, therefor On title page 2, in column 1, under "(56) Other Publications", line 13, delete "L," and insert --L.,-- therefor On title page 2, in column 1, under "(56) Other Publications", line 16, delete "F," and insert --F.,-- therefor On title page 2, in column 2, under "(56) Other Publications", line 1, delete "H," and insert --H.,-- therefor On title page 2, in column 2, under "(56) Other Publications", line 8, delete "S," and insert --S.,-- therefor On title page 2, in column 2, under "(56) Other Publications", line 11, delete "A," and insert --A.,-- therefor On title page 2, in column 2, under "(56) Other Publications", line 15, delete "S," and insert --S.,-- therefor On title page 2, in column 2, under "(56) Other Publications", line 22, delete "S," and insert --S.,-- therefor On title page 2, in column 2, under "(56) Other Publications", line 28, delete "A," and insert --A.,-- therefor On title page 2, in column 2, under "(56) Other Publications", line 32, before "U.S.", insert --"--, therefor On title page 2, in column 2, under "(56) Other Publications", line 32, after "2013", insert --"--, therefor On title page 2, in column 2, under "(56) Other Publications", line 34, before "U.S.", insert --"--, therefor On title page 2, in column 2, under "(56) Other Publications", line 35, after "2012", insert --"--, therefor On title page 2, in column 2, under "(56) Other Publications", line 36, before "European.", insert --"--, therefor On title page 2, in column 2, under "(56) Other Publications", line 37, after "2013", insert --"--, therefor On title page 2, in column 2, under "(56) Other Publications", line 38, before "International", insert --"--, therefor On title page 2, in column 2, under "(56) Other Publications", line 39, after "2009", insert --"--, therefor On title page 2, in column 2, under "(56) Other Publications", line 41, before "International", insert --"--, therefor On title page 2, in column 2, under "(56) Other Publications", line 42, after "2009", insert --"--, therefor On title page 2, in column 2, under "(56) Other Publications", line 43, before "International", insert --"--, therefor On title page 2, in column 2, under "(56) Other Publications", line 44, after "2009", insert --"--, therefor On title page 2, in column 2, under "(56) Other Publications", line 52, before "U.S.", insert --"--, therefor On title page 2, in column 2, under "(56) Other Publications", line 53, after "2012", insert --"--, therefor On title page 2, in column 2, under "(56) Other Publications", line 54, before "U.S.", insert --"--, therefor On title page 2, in column 2, under "(56) Other Publications", line 55, after "2012", insert --"--, therefor On title page 2, in column 2, under "(56) Other Publications", line 56, before "U.S.", insert --"--, therefor On title page 2, in column 2, under "(56) Other Publications", line 57, after "2012", insert --"--, therefor On title page 2, in column 2, under "(56) Other Publications", line 58, before "U.S.", insert --"--, therefor On title page 2, in column 2, under "(56) Other Publications", line 58, after "2013", insert --"--, therefor On title page 2, in column 2, under "(56) Other Publications", line 60, before "U.S.", insert --"--, therefor On title page 2, in column 2, under "(56) Other Publications", line 61, after "2012", insert --"--, therefor On title page 2, in column 2, under "(56) Other Publications", line 62, before "U.S.", insert --"--, therefor On title page 2, in column 2, under "(56) Other Publications", line 63, after "2012", insert --"--, therefor On title page 2, in column 2, under "(56) Other Publications", line 64, before "U.S.", insert --"--, therefor On title page 2, in column 2, under "(56) Other Publications", line 65, after "2012", insert --"--, therefor On title page 2, in column 2, under "(56) Other Publications", line 66, before "U.S.", insert --"--, therefor On title page 2, in column 2, under "(56) Other Publications", line 67, after "2012", insert --"--, therefor On title page 2, in column 2, under "(56) Other Publications", line 68, before "U.S.", insert --"--, therefor On title page 2, in column 2, under "(56) Other Publications", line 69, after "2012", insert --"--, therefor On title page 2, in column 2, under "(56) Other Publications", line 70, before "U.S.", insert --"--, therefor On title page 2, in column 2, under "(56) Other Publications", line 70, after "2012", insert --"--, therefor On title page 2, in column 2, under "(56) Other Publications", line 72, before "U.S.", insert --"--, therefor On title page 2, in column 2, under "(56) Other Publications", line 73, after "2012", insert --"--, therefor On title page 3, in column 1, under "(56) Other Publications", line 1, before "U.S.", insert --"--, therefor On title page 3, in column 1, under "(56) Other Publications", line 1, after "2009", insert --"--, therefor On title page 3, in column 1, under "(56) Other Publications", line 2, before "U.S.", insert --"--, therefor On title page 3, in column 1, under "(56) Other Publications", line 2, after "2012", insert --"--, therefor On title page 3, in column 1, under "(56) Other Publications", line 4, before "U.S.", insert --"--, therefor On title page 3, in column 1, under "(56) Other Publications", line 5, after "2012", insert --"--, therefor On title page 3, in column 1, under "(56) Other Publications", line 6, before "U.S.", insert --"--, therefor On title page 3, in column 1, under "(56) Other Publications", line 7, after "2013", insert --"--, therefor On title page 3, in column 1, under "(56) Other Publications", line 8, before "U.S.", insert --"--, therefor On title page 3, in column 1, under "(56) Other Publications", line 9, after "2012", insert --"--, therefor On title page 3, in column 1, under "(56) Other Publications", line 10, before "U.S.", insert --"--, therefor On title page 3, in column 1, under "(56) Other Publications", line 11, after "2011", insert --"--, therefor On title page 3, in column 1, under "(56) Other Publications", line 24, delete "[125I]Iododeoxyuridine" and insert --[$^{125}$I]-Iododeoxyuridine--, therefor On title page 3, in column 2, under "(56) Other Publications", line 4, delete "D," and insert --D.,--, therefor

CERTIFICATE OF CORRECTION (continued)
U.S. Pat. No. 8,600,479 B2

On title page 3, in column 2, under "(56) Other Publications", line 12, delete "W," and insert --W.,-- therefor On title page 3, in column 2, under "(56) Other Publications", line 15, delete "A," and insert --A.,-- therefor On title page 3, in column 2, under "(56) Other Publications", line 17, delete "A," and insert --A.,-- therefor On title page 3, in column 2, under "(56) Other Publications", line 21, delete "J," and insert --J.,-- therefor On title page 3, in column 2, under "(56) Other Publications", line 25, delete "S," and insert --S.,-- therefor On title page 3, in column 2, under "(56) Other Publications", line 28, delete "H," and insert --H.,-- therefor On title page 3, in column 2, under "(56) Other Publications", line 30, After "301-9.", insert --¶"U.S. Appl. No. 12/375,583, Non Final Office Action mailed Oct. 30, 2013", 22 pgs.

"European Application Serial No. 07836227.4, Extended European Search Report mailed Oct. 1, 2013", 5 pgs.--, therefor In the Claims In column 28, line 66, in claim 34, delete "bio active" and insert --bioactive--, therefor